(12) United States Patent
Nash

(10) Patent No.: US 9,175,056 B2
(45) Date of Patent: *Nov. 3, 2015

(54) BIS-SULFHYDRYL MACROCYCLIZATION SYSTEMS

(71) Applicant: Aileron Therapeutics, Inc., Cambridge, MA (US)

(72) Inventor: Huw M. Nash, Concord, MA (US)

(73) Assignee: Aileron Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,367

(22) Filed: Nov. 1, 2013

(65) Prior Publication Data

US 2014/0135473 A1    May 15, 2014

Related U.S. Application Data

(63) Continuation of application No. 12/690,076, filed on Jan. 19, 2010, now Pat. No. 8,609,809, which is a continuation of application No. 11/957,325, filed on Dec. 14, 2007, now Pat. No. 7,960,506.

(60) Provisional application No. 60/874,819, filed on Dec. 14, 2006.

(51) Int. Cl.
| | | |
|---|---|---|
| A61K 38/12 | (2006.01) |
| A61K 38/10 | (2006.01) |
| A61K 45/06 | (2006.01) |
| C07K 7/08 | (2006.01) |
| C07K 7/64 | (2006.01) |
| C07K 14/47 | (2006.01) |
| C07K 14/68 | (2006.01) |
| C07K 14/705 | (2006.01) |
| C07K 1/113 | (2006.01) |

(52) U.S. Cl.
CPC ............ *C07K 14/4747* (2013.01); *C07K 1/1133* (2013.01); *C07K 14/68* (2013.01); *C07K 14/705* (2013.01)

(58) Field of Classification Search
CPC ....... A61K 38/12; A61K 38/10; A61K 45/06; C07K 14/4746; C07K 1/113; C07K 14/705; C07K 7/08; C07K 7/64
USPC ........ 514/21.1, 21.4; 530/326, 317, 323, 324, 530/327, 345
See application file for complete search history.

(56) References Cited

U.S. PATENT DOCUMENTS

| | | |
|---|---|---|
| 4,000,259 A | 12/1976 | Garsky |
| 4,191,754 A | 3/1980 | Veber et al. |
| 4,438,270 A | 3/1984 | Bey et al. |
| 5,364,851 A | 11/1994 | Joran |
| 5,446,128 A | 8/1995 | Kahn |
| 5,622,852 A | 4/1997 | Korsmeyer |
| 5,650,133 A | 7/1997 | Carvalho et al. |
| 5,663,316 A | 9/1997 | Xudong |
| 5,708,136 A | 1/1998 | Burrell et al. |
| 5,811,515 A | 9/1998 | Grubbs et al. |
| 5,817,752 A | 10/1998 | Yu |
| 5,824,483 A | 10/1998 | Houston, Jr. et al. |
| 5,834,209 A | 11/1998 | Korsmeyer |
| 5,840,833 A | 11/1998 | Kahn et al. |
| 5,856,445 A | 1/1999 | Korsmeyer |
| 5,859,184 A | 1/1999 | Kahn et al. |
| 5,955,593 A | 9/1999 | Korsmeyer |
| 5,965,703 A | 10/1999 | Horne et al. |
| 5,998,583 A | 12/1999 | Korsmeyer |
| 6,031,073 A | 2/2000 | Yu |
| 6,153,391 A | 11/2000 | Picksley et al. |
| 6,169,073 B1 | 1/2001 | Halazonetis et al. |
| 6,204,361 B1 | 3/2001 | Carpino et al. |
| 6,271,198 B1 | 8/2001 | Braisted et al. |
| 6,287,787 B1 | 9/2001 | Houghten et al. |
| 6,326,354 B1 | 12/2001 | Gross et al. |
| 6,613,874 B1 | 9/2003 | Mazur et al. |
| 6,686,148 B1 | 2/2004 | Shen et al. |
| 6,703,382 B2 | 3/2004 | Wang et al. |
| 6,713,280 B1 | 3/2004 | Huang et al. |
| 7,064,193 B1 | 6/2006 | Cory et al. |
| 7,083,983 B2 | 8/2006 | Lane et al. |
| 7,115,372 B2 | 10/2006 | Shen et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,705,118 B2 | 4/2010 | Arora et al. |
| 7,723,469 B2 | 5/2010 | Walensky et al. |
| 7,786,072 B2 | 8/2010 | Verdine et al. |

(Continued)

FOREIGN PATENT DOCUMENTS

| | | |
|---|---|---|
| CN | 1583730 A | 2/2005 |
| EP | 0467699 A2 | 1/1992 |

(Continued)

OTHER PUBLICATIONS

Office action dated Jul. 21, 2014 for U.S. Appl. No. 13/370,057.
U.S. Appl. No. 14/068,844, filed Oct. 31, 2013, Verdine et al.
U.S. Appl. No. 14/156,350, filed Jan. 15, 2014, Nash et al.
Andrews, et al. Forming Stable Helical Peptides Using Natural and Artificial Amino Acids. Tetrahedron. 1999; 55:11711-11743.
Angell, et al. Peptidomimetics via copper-catalyzed azide-alkyne cycloadditions. Chem Soc Rev. Oct. 2007;36(10):1674-89.
Angell, et al. Ring closure to beta-turn mimics via copper-catalyzed azide/alkyne cycloadditions. J Org Chem. Nov. 11, 2005;70(23):9595-8.
Baell, et al. Prospects for targeting the Bcl-2 family of proteins to develop novel cytotoxic drugs. Biochem Pharm. 2002; 64:851-863.

(Continued)

*Primary Examiner* — Julie Ha
(74) *Attorney, Agent, or Firm* — Wilson Sonsini Goodrich & Rosati

(57) ABSTRACT

Peptidomimetic macrocycles and methods for their preparation and use, as well as amino acid analogs and macrocycle-forming linkers, and kits useful in their production are described.

21 Claims, 1 Drawing Sheet

(56) References Cited

U.S. PATENT DOCUMENTS

| | | |
|---|---|---|
| 7,960,506 B2 | 6/2011 | Nash |
| 7,981,998 B2 | 7/2011 | Nash |
| 7,981,999 B2 | 7/2011 | Nash |
| 8,071,541 B2 | 12/2011 | Arora et al. |
| 8,198,405 B2 | 6/2012 | Walensky et al. |
| 8,324,428 B2 | 12/2012 | Verdine et al. |
| 8,389,484 B2 | 3/2013 | Shen et al. |
| 8,399,405 B2 | 3/2013 | Nash et al. |
| 8,524,653 B2 | 9/2013 | Nash et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 | 10/2014 | Guerlavais et al. |
| 8,871,899 B2 | 10/2014 | Wang et al. |
| 8,889,632 B2 | 11/2014 | Bernal et al. |
| 8,895,699 B2 | 11/2014 | Verdine et al. |
| 8,927,500 B2 | 1/2015 | Guerlavais et al. |
| 8,987,414 B2 | 3/2015 | Guerlavais et al. |
| 9,023,988 B2 | 5/2015 | Nash |
| 2003/0166138 A1 | 9/2003 | Kinsella et al. |
| 2004/0106159 A1 | 6/2004 | Kern et al. |
| 2004/0106548 A1 | 6/2004 | Schmidt et al. |
| 2004/0152708 A1 | 8/2004 | Li et al. |
| 2004/0171809 A1 | 9/2004 | Korsmeyer et al. |
| 2005/0119167 A1 | 6/2005 | Abbenante et al. |
| 2005/0222427 A1 | 10/2005 | Sharpless et al. |
| 2005/0250680 A1 | 11/2005 | Walensky et al. |
| 2006/0014675 A1 | 1/2006 | Arora et al. |
| 2006/0073518 A1 | 4/2006 | Timmerman et al. |
| 2006/0111411 A1 | 5/2006 | Cooper et al. |
| 2006/0293380 A1 | 12/2006 | Nantermet et al. |
| 2007/0020620 A1 | 1/2007 | Finn et al. |
| 2008/0213175 A1 | 9/2008 | Kolb et al. |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0275519 A1 | 11/2009 | Nash et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0210515 A1 | 8/2010 | Nash et al. |
| 2010/0216688 A1 | 8/2010 | Nash et al. |
| 2010/0234563 A1 | 9/2010 | Arora et al. |
| 2010/0273704 A1 | 10/2010 | Korsmeyer et al. |
| 2010/0298201 A1 | 11/2010 | Nash et al. |
| 2011/0028753 A1 | 2/2011 | Verdine et al. |
| 2011/0046043 A1 | 2/2011 | Wang et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0245175 A1 | 10/2011 | Arora et al. |
| 2011/0250685 A1 | 10/2011 | Nash |
| 2011/0263815 A1 | 10/2011 | Nash |
| 2012/0040889 A1 | 2/2012 | Nash et al. |
| 2012/0082636 A1 | 4/2012 | Walensky et al. |
| 2012/0101047 A1 | 4/2012 | Nash et al. |
| 2012/0115783 A1 | 5/2012 | Nash et al. |
| 2012/0115793 A1 | 5/2012 | Nash et al. |
| 2012/0178700 A1 | 7/2012 | Nash et al. |
| 2012/0190818 A1 | 7/2012 | Nash et al. |
| 2012/0264674 A1 | 10/2012 | Nash et al. |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0072439 A1 | 3/2013 | Nash et al. |
| 2013/0123169 A1 | 5/2013 | Kawahata et al. |
| 2013/0123196 A1 | 5/2013 | Arora et al. |
| 2013/0211046 A1 | 8/2013 | Verdine et al. |
| 2014/0011979 A1 | 1/2014 | Verdine et al. |
| 2014/0051828 A1 | 2/2014 | Arora et al. |
| 2014/0128581 A1 | 5/2014 | Darlak et al. |
| 2014/0135255 A1 | 5/2014 | Nash et al. |
| 2014/0162339 A1 | 6/2014 | Verdine et al. |
| 2014/0296160 A1 | 10/2014 | Walensky et al. |
| 2014/0323701 A1 | 10/2014 | Nash et al. |
| 2014/0378390 A1 | 12/2014 | Guerlavais et al. |
| 2015/0051155 A1 | 2/2015 | Guerlavais et al. |

FOREIGN PATENT DOCUMENTS

| | | |
|---|---|---|
| EP | 0467699 A3 | 2/1993 |
| EP | 1452868 A2 | 9/2004 |
| EP | 1541692 A1 | 6/2005 |
| EP | 1602663 A1 | 12/2005 |
| EP | 1597585 B1 | 6/2011 |
| WO | WO 89/09233 A1 | 10/1989 |
| WO | 9213878 A2 | 8/1992 |
| WO | WO 93/01203 A1 | 1/1993 |
| WO | WO 94/25482 A1 | 11/1994 |
| WO | WO 95/00534 A1 | 1/1995 |
| WO | WO 96/28449 A1 | 9/1996 |
| WO | 9634878 A1 | 11/1996 |
| WO | WO 97/00267 A1 | 1/1997 |
| WO | WO 97/30072 A1 | 8/1997 |
| WO | WO 98/46631 A1 | 10/1998 |
| WO | WO 02/072597 A2 | 9/2002 |
| WO | WO 03/059933 A2 | 7/2003 |
| WO | WO 03/070892 A2 | 8/2003 |
| WO | WO 03/059933 A3 | 1/2004 |
| WO | 2004026896 A2 | 4/2004 |
| WO | WO 2004/058804 A1 | 7/2004 |
| WO | WO 2004/077062 A2 | 9/2004 |
| WO | WO 03/070892 A3 | 11/2004 |
| WO | WO 2004/077062 A3 | 1/2005 |
| WO | WO 2005/007675 A2 | 1/2005 |
| WO | WO 2004/077062 A3 | 2/2005 |
| WO | WO 2005/012335 A1 | 2/2005 |
| WO | WO 2005/040202 A2 | 5/2005 |
| WO | WO 2005/044839 A2 | 5/2005 |
| WO | WO 2005/040202 A3 | 6/2005 |
| WO | WO 2005/007675 A3 | 7/2005 |
| WO | WO 2005/044839 A3 | 7/2005 |
| WO | WO 2005/090388 A1 | 9/2005 |
| WO | 2005118620 A2 | 12/2005 |
| WO | WO 2006/078161 A1 | 7/2006 |
| WO | WO 2008/013454 A2 | 1/2008 |
| WO | 2008061192 A2 | 5/2008 |
| WO | 2008076904 A1 | 6/2008 |
| WO | WO 2008/074895 A1 | 6/2008 |
| WO | 2008095063 A1 | 8/2008 |
| WO | 2008104000 A2 | 8/2008 |
| WO | 2008121767 A2 | 10/2008 |
| WO | 2008137633 A2 | 11/2008 |
| WO | WO 2009/089004 A1 | 7/2009 |
| WO | 2009099677 A2 | 8/2009 |
| WO | 2009110952 A2 | 9/2009 |
| WO | 2009126292 A2 | 10/2009 |
| WO | 2009149214 A2 | 12/2009 |
| WO | 2010033879 A2 | 3/2010 |
| WO | 2010034026 A1 | 3/2010 |
| WO | 2010034028 A1 | 3/2010 |
| WO | 2010034029 A1 | 3/2010 |
| WO | 2010034031 A1 | 3/2010 |
| WO | 2010034032 A2 | 3/2010 |
| WO | 2010034034 A1 | 3/2010 |
| WO | 2010060112 A1 | 5/2010 |
| WO | 2010083347 A2 | 7/2010 |
| WO | 2011008260 A2 | 1/2011 |
| WO | 2011038049 A1 | 3/2011 |
| WO | 2011047215 A1 | 4/2011 |
| WO | 2012021874 A1 | 2/2012 |
| WO | 2012021875 A1 | 2/2012 |
| WO | 2012021876 A2 | 2/2012 |
| WO | 2012122059 A1 | 9/2012 |
| WO | 2012173846 A2 | 12/2012 |
| WO | 2013033645 A1 | 3/2013 |
| WO | 2013059525 A1 | 4/2013 |
| WO | 2013059530 A2 | 4/2013 |

(56) References Cited

FOREIGN PATENT DOCUMENTS

| WO | 2013123266 A1 | 8/2013 |
|---|---|---|
| WO | 2013123267 A1 | 8/2013 |
| WO | 2014071241 A1 | 5/2014 |
| WO | 2014138429 A2 | 9/2014 |

OTHER PUBLICATIONS

Barker, et al. Cyclic RGD peptide analogues as antiplatelet antithrombotics. J Med Chem. May 29, 1992;35(11):2040-8. (Abstract only).

Berendsen, H. A glimpse of the Holy Grail? Science. Oct. 23, 1998;282(5389):642-3.

Blackwell, et al. Highly effiecient synthesis of covalently cross-linked peptide helices by ring-closing metathesis. Agnew Chem Int Ed. 1998;37(23):3281-3284.

Blackwell, et al. Ring-closing metathesis of olefinic peptides: design, synthesis, and structural characterization of macrocyclic helical peptides. J Org Chem. Aug. 10, 2001;66(16):5291-302.

Bock, et al. 1,2,3-Triazoles as peptide bond isosteres: synthesis and biological evaluation of cyclotetrapeptide mimics Org Biomol Chem. Mar. 21, 2007;5(6):971-5.

Bradley, et al. Limits of cooperativity in a structurally modular protein: response of the Notch ankyrin domain to analogous alanine substitutions in each repeat. J Mol Biol. Nov. 22, 2002;324(2):373-86.

Brunel, et al. Synthesis of constrained helical peptides by thioether ligation: application to analogs of gp41. Chem Commun (Camb). May 28, 2005;(20):2552-4.

Burrage, et al. Biomimetic synthesis of lantibiotics. Chemistry. Apr. 14, 2000;6(8):1455-66.

Cantel, et al. Synthesis and Conformational Analysis of a Cyclic Peptide Obtained via *i* to *i*+4 Intramolecular Side-Chain to Side-Chain Azide-Alkyne 1,3-Dipolar Cycloaddition. JOC Featured Article. Published on the web May 20, 2008.

CAS Registry No. 2176-37-6, STN Entry Date Nov. 16, 1984.
CAS Registry No. 2408-85-7, STN Entry Date Nov. 16, 1984.
CAS Registry No. 4727-05-3, STN Entry Date Nov. 16, 1984.
CAS Registry No. 561321-72-0, STN Entry Date Aug. 6, 2003.
CAS Registry No. 721918-14-5, STN Entry Date Aug. 4, 2004.

Choi, et al. Application of azide-alkyne cycloaddition 'click chemistry' for the synthesis of Grb2 SH2 domain-binding macrocycles. Bioorg Med Chem Lett. Oct. 15, 2006;16(20):5265-9.

Chu, et al. Peptide-formation on cysteine-containing peptide scaffolds. Orig Life Evol Biosph. Oct. 1999;29(5):441-9.

Cline, et al. Effects of As(III) binding on alpha-helical structure. J Am Chem Soc. Mar. 12, 2003;125(10):2923-9.

Definition of Analog from http://cancerweb.ncl.ac.uk/cgi-bin/omd?query=analog. pp. 1-5. Accessed Jul. 7, 2005.

Deng, et al. Cross-Coupling Reaction of Iodo-1,2,3-triazoles Catalyzed by Palladium. Synthesis 2005(16): 2730-2738.

Designing Custom Peptides. From SIGMA Genosys. pp. 1-2. Accessed Dec. 16, 2004.

Dimartino et al. Solid-phase synthesis of hydrogen-bond surrogate-derived alpha-helices. Org Lett. Jun. 9, 2005;7(12):2389-92.

Erlanson, et al. Facile synthesis of cyclic peptides containing di-, tri-, tetra-, and Pentasulfides. Tetrahedron Letters. 1998; 39(38):6799-6802.

European search report and search opinion dated Jun. 5, 2013 for EP Application No. 12174833.

European search report and search opinion dated Jun. 6, 2013 for EP Application No. 12174832.

European search report and search opinion dated Dec. 17, 2010 for Application No. 07869296.9.

European search report dated Mar. 2, 2010 for Application No. 8730678.3.

Feng et al. Solid-phase SN2 macrocyclization reactions to form beta-turn mimics Org Lett. Jul. 15, 1999;1(1):121-4.

Galande, et al. Thioether side chain cyclization for helical peptide formation: inhibitors of estrogen receptor-coactivator interactions. Journal of Peptide Research. 2004; 63(3): 297-302.

Galande, et al. An effective method of on-resin disulfide bond formation in peptides. J Comb Chem. Mar.-Apr. 2005;7(2):174-7.

Goncalves, et al. On-resin cyclization of peptide ligands of the Vascular Endothelial Growth Factor Receptor 1 by copper(I)-catalyzed 1,3-dipolar azide-alkyne cycloaddition. Bioorg Med Chem Lett. Oct. 15, 2007;17(20):5590-4.

Hanessian, et al. Structure-based design and synthesis of macroheterocyclic peptidomimetic inhibitors of the aspartic protease beta-site amyloid precursor protein cleaving enzyme (BACE). J Med Chem. Jul. 27, 2006;49(15):4544-67.

Hara, S. et al. 'Synthetic studies on halopeptins, anti-inflammatory cyclodepsipeptides', Peptide Science. 2006 (vol. date 2005), 42nd, pp. 39-42.

Hein, et al. Copper(I)-Catalyzed Cycloaddition of Organic Azides and 1-Iodoalkynes. Angew Chem Int Ed Engl. 2009;48(43):8018-21.

International search report dated Apr. 28, 2008 for PCT Application No. US2007/87615.

International search report dated Sep. 25, 2008 for PCT Application No. US2008/54922.

Jackson, et al. General approach to the synthesis of short α-helical peptides. Journal of the American Chemical Society. 1991;113(24) 9391-9392.

Jin, et al. Structure-based design, synthesis, and activity of peptide inhibitors of RGS4 GAP activity. Methods Enzymol. 2004;389:266-77.

Jin, et al. Structure-based design, synthesis, and pharmacologic evaluation of peptide RGS4 inhibitors. J Pept Res. Feb. 2004;63(2):141-6.

Johannasson, et al. Vinyl sulfide cyclized analogues of angiotensin II with high affinity and full agonist activity at the AT(1) receptor. J Med Chem. Apr. 25, 2002;45(9):1767-77.

Kanan et al. Reaction discovery enabled by DNA-templated synthesis and in vitro selection. Nature. Sep. 30, 2004;431(7008):545-9.

Kedrowski, B.L. et al. 'Thiazoline ring formation from 2-methylcysteines and 2-halomethylalanines', Heterocycles. 2002, vol. 58, pp. 601-634.

Kudaj, et al. An efficient synthesis of optically pure alpha-alkyl-beta-azido- and alpha-alkyl-beta-aminoalanines via ring opening of 3-amino-3-alkyl-2-oxetanones. Tetrahedron Letters. 2007; 48:6794-6797.

Li, et al. A Convenient Preparation of 5-Iodo-1,4-disubstituted-1,2,3-triazole: Multicomponent One-Pot Reaction of Azide and Alkyne Mediated by CuI—NBS. J. Org. Chem. 2008;73(9):3630-3633.

Li, et al. Structure-based design of thioether-bridged cyclic phosphopeptides binding to Grb2-SH2 domain. Bioorg Med Chem Lett. Mar. 10, 2003;13(5):895-9.

Mai, et al. A proapoptotic peptide for the treatment of solid tumors. Cancer Research. 2001; 61:7709-7712.

Mangold, et al. Azidoalanine mutagenicity in *Salmonella*: effect of homologation and alpha-Mutat Res. Feb. 1989;216(1):27-33.methyl substitution.

Martin, et al. Thermal [2+2+] intramolecular cycloadditions of fuller-1,6-enynes. Angew Chem Int Ed Engl. Feb. 20, 2006;45(9):1439-42.

McNamara, et al. Peptides Constrained by an Aliphatic Linkage between Two Cα Sites: Design, Synthesis, and Unexpected Conformational Properties of an i,(i+4)-Linked Peptide. J. Org. Chem. 2001; 66:4585-4595.

Mosberg, et al. Dithioether-Constaining Cyclic Peptides. J. Am. Chem. Soc. 1985; 107; 2987-2988.

Mulqueen et al. Synthesis of the thiazoline-based siderophore (S)-desferrithiocin. 1993;48(24):5359-5364.

Mustapa, et al. Synthesis of a Cyclic Peptide Containing Norlanthionine: Effect of the Thioether Bridge on Peptide Conformation. J. Org. Chem. 2003; 68: 8193-8198.

Ngo, et al. Computational complexity, protein structure prediction, and the levinthal paradox. The Protein Folding Problem and Tertiary Structure Prediction. K. Merc Jr. and S. Le Grand Edition. 1994, pp. 491-495.

Office action dated Mar. 18, 2013 for U.S. Appl. No. 13/097,930.
Office action dated Apr. 26, 2012 for U.S. Appl. No. 13/097,930.

(56) References Cited

OTHER PUBLICATIONS

Office action dated May 10, 2010 for U.S. Appl. No. 11/957,325.
Office action dated May 19, 2010 for U.S. Appl. No. 12/140,241.
Office action dated Jun. 28, 2013 for U.S. Appl. No. 13/370,057.
Office action dated Jul. 15, 2013 for U.S. Appl. No. 13/570,146.
Office action dated Jul. 30, 2013 for U.S. Appl. No. 13/097,930.
Office action dated Aug. 10, 2009 for U.S. Appl. No. 11/957,325.
Office action dated Aug. 11, 2009 for U.S. Appl. No. 12/140,241.
Office action dated Aug. 19, 2010 for U.S. Appl. No. 12/037,041.
Office action dated Oct. 15, 2012 for U.S. Appl. No. 13/097,930.
Office action dated Dec. 13, 2012 for U.S. Appl. No. 12/690,076.
Or, et al. Cysteine alkylation of unprotected peptides: Synthesis of a carbavasopressin analogue by intramolecular cysteine alkylation. 1991;56(9):3146-3149.
Pattenden, et al. Enantioselective synthesis of 2-alkyl substituted cysteines. 1993;49(10):2131-2138.
Pattenden, et al. Naturally occurring linear fused thiazoline-thiazole containing metabolites: total synthesis of (−)-didehydromirabazole A, a cytotoxic alkaloid from blue-green algae. J Chem Soc. 1993;14:1629-1636.
Punna, et al. Head-to-tail peptide cyclodimerization by copper-catalyzed azide-alkyne cycloaddition. Angew Chem Int Ed Engl. Apr. 8, 2005;44(15):2215-20.
Rasmussen, et al. Ruthenium-catalyzed cycloaddition of aryl azides and alkynes. Org Lett. Dec. 20, 2007;9(26):5337-9.
Rink, et al. Lantibiotic Structures as Guidelines for the Design of Peptides That Can Be Modified by Lantibiotic Enzymes. Biochemistry. 2005; 44:8873-8882.
Roice, et al. High Capacity Poly(ethylene glycol) Based Amino Polymers for Peptide and Organic Synthesis. QSAR & Combinatorial Science. 2004;23(8):662-673.
Rojo, et al. Macrocyclic peptidomimetic inhibitors of β-secretase (BACE): First X-ray structure of a macrocyclic peptidomimetic-BACE complex. Bioorg. Med. Chem. Lett. 2006; 16:191-195.
Roof, et al. Mechanism of action and structural requirements of constrained peptide inhibitors of RGS proteins. Chem Biol Drug Des. Apr. 2006;67(4):266-74.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rudinger, J. Characteristics of the amino acids as components of a peptide hormone sequence. Peptide Hormones. JA Parsons Edition. University Park Press. Jun. 1976, pp. 1-7.
Schafmeister, et al. An all-hydrocarbon cross-linking system for enhancing the helicity and metabolic stability of peptides. Journal of the American Chemical Society. 2000;122(24):5891-5892.
Schinzel, et al. The phosphate recognition site of *Escherichia coli* maltodextrin phosphorylase. FEBS Lett. Jul. 29, 1991;286(1-2):125-8.
Scott, et al. A Solid-Phase Synthetic Route to Unnatural Amino Acids with Diverse Side-Chain Substitutions. Journal of Organic Chemistry. 2002, vol. 67, No. 9, pp. 2960-2969.
Seebeck, et al. Ribosomal synthesis of dehydroalanine-containing peptides. J Am Chem Soc. Jun. 7, 2006;128(22):7150-1.
Shi, et al. The role of arsenic-thiol interactions in metalloregulation of the ars operant. J Biol Chem. Apr. 19, 1996;271(16):9291-7.
Singh, et al. Efficient asymmetric synthesis of (S)- and (R)-N-Fmoc-S-trityl-alpha-methylcysteine using camphorsultam as a chiral auxiliary.. J Org Chem. Jun. 25, 2004;69(13):4551-4.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S 39.
Solution phase synthesis from http://www.combichemistry.com/solution_phase_synthesis.html. P.1. Accessed Aug. 6, 2009.
Szewczuk, et al. Synthesis and Biological activity of new conformationally restricted analogues of pepstatin. Int. J. Peptide Protein. Res. 1992; 40:233-242.
Taylor, J. The synthesis and study of side-chain lactam-bridged peptides. Biopolymers. 2002;66(1):49-75.
Tornoe, et al. Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Torres, et al. Peptide tertiary structure nucleation by side-chain crosslinking with metal complexation and double "click" cycloaddition. Chembiochem. Jul. 21, 2008;9(11):1701-5.
Van Maarseveen, et al. Efficient route to C2 symmetric heterocyclic backbone modified cyclic peptides. Org Lett. Sep. 29, 2005;7(20):4503-6.
Voet, et al. Biochemistry, Second Edition. John Wiley & Sons, Inc. 1995, pp. 235-241.
Walensky, et al. Activation of apoptosis in vivo by a hydrocarbon-stapled BH3 helix. Science. Sep. 3, 2004;305(5689):1466-70.
Walker, et al. General method for the synthesis of cyclic peptidomimetic compounds. Tetrahedron Letters. 2001; 42(34):5801-5804.
Wang, et al. Cell permeable Bcl-2 binding peptides: a chemical approach to apoptosis induction in tumor cells. Cancer Research. 2000; 60:1498-1502.
Wang, et al. Enhanced metabolic stability and protein-binding properties of artificial alpha helices derived from a hydrogen-bond surrogate: application to Bcl-xL. Angew Chem Int Ed Engl. 2005; 44: 6525-6529.
Wels, et al. Synthesis of a novel potent cyclic peptide MC4-ligand by ring-closing metathesis. Bioorg. Med. Chem. Lett. 2005; 13: 4221-4227.
Wu, et al. Regiospecific Synthesis of 1,4,5-Trisubstituted-1,2,3-triazole via One-Pot Reaction Promoted by Copper(I) Salt. Synthesis. 2005(8): 1314-1318.
Wu, et al. Studies on New Strategies for the Synthesis of Oligomeric 1,2,3-Triazoles. Synlett 2006(4): 0645-0647.
Yang, et al. Synthesis and helical structure of lactam bridged BH3 peptides derived from pro-apoptotic Bcl-2 family proteins. Bioorg Med Chem Lett. 2004; 14:1403-1406.
Zhang, et al. Ruthenium-catalyzed cycloaddition of alkynes and organic azides. J Am Chem Soc. Nov. 23, 2005;127(46):15998-9.
Office action dated Feb. 4, 2014 for U.S. Appl. No. 13/370,057.
Co-pending U.S. Appl. No. 13/494,846, filed Jun. 12, 2012.
Co-pending U.S. Appl. No. 13/655,442, filed Oct. 18, 2010.
Co-pending U.S. Appl. No. 13/784,345, filed Mar. 4, 2013.
Co-pending U.S. Appl. No. 14/325,933, filed Jul. 8, 2014.
Co-pending U.S. Appl. No. 14/483,905, filed Sep. 11, 2014.
Co-pending U.S. Appl. No. 14/608,641, filed Jan. 29, 2015.
Co-pending U.S. Appl. No. 14/677,679, filed Apr. 2, 2015.
Marshall et al., Back to the future: ribonuclease A. Biopolymers. 2008;90(3):259-77.
Muir, Semisynthesis of proteins by expressed protein ligation. Annu Rev Biochem. 2003;72:249-89. Epub Feb. 27, 2003.
"Notice of allowance dated Jan. 7, 2015 for U.S. Appl. No. 13/370,057."
Office action dated Oct. 31, 2014 for U.S. Appl. No. 13/370,057.
Co-pending U.S. Appl. No. 14/718,288, filed May 21, 2015.

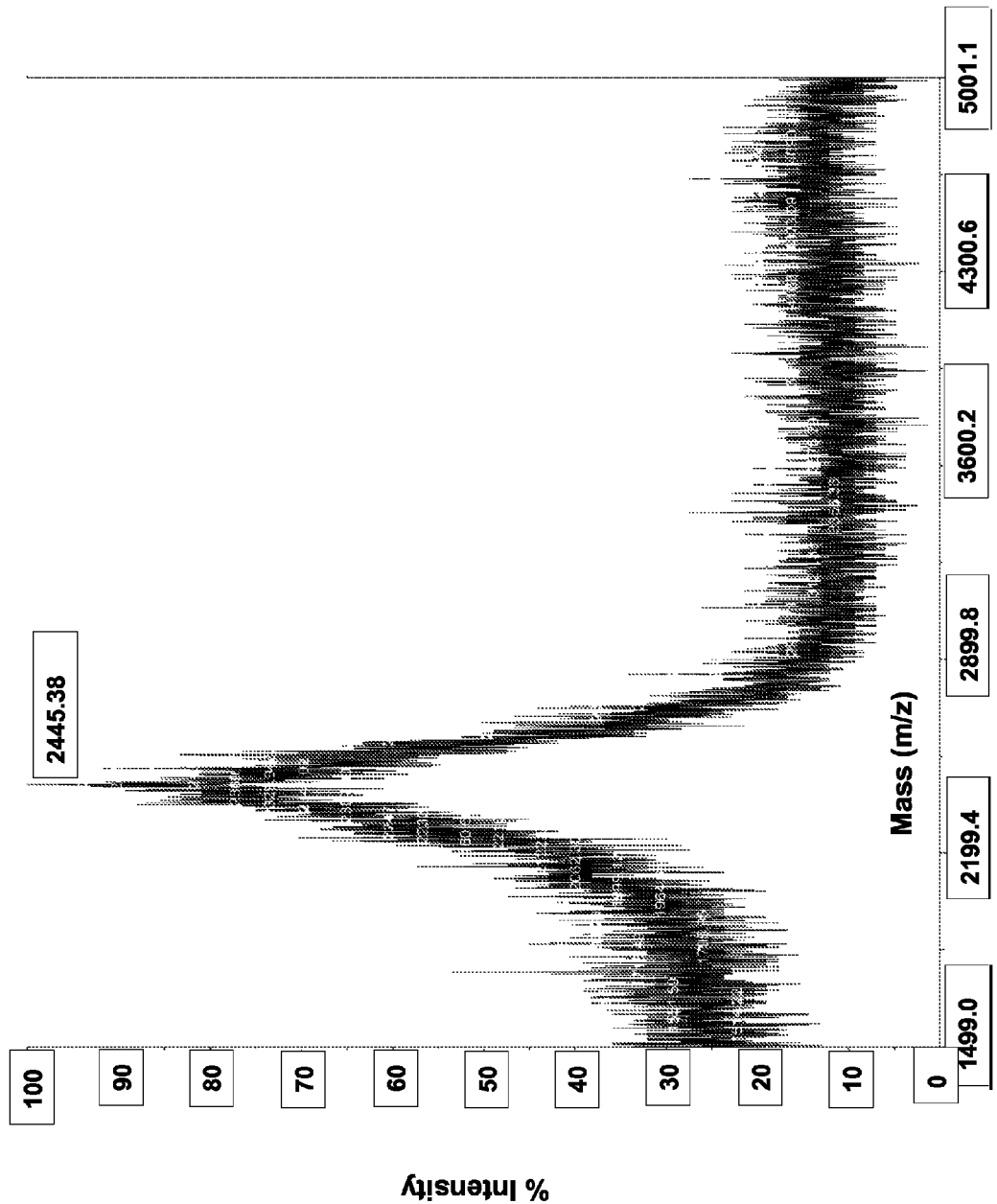

SEQUENCE LISTING

<160> NUMBER OF SEQ ID NOS: 100

<210> SEQ ID NO 1

```
<211> LENGTH: 19
<212> TYPE: PRT
<213> ORGANISM: Homo sapiens

<400> SEQUENCE: 1

Pro Leu Ser Gln Glu Thr Phe Ser Asp Leu Trp Lys Leu Leu Pro Glu
1               5                   10                  15

Asn Asn Val

<210> SEQ ID NO 2
<211> LENGTH: 25
<212> TYPE: PRT
<213> ORGANISM: Homo sapiens

<400> SEQUENCE: 2

Gln Glu Asp Ile Ile Arg Asn Ile Ala Arg His Leu Ala Gln Val Gly
1               5                   10                  15

Asp Ser Met Asp Arg Ser Ile Pro Pro
            20                  25

<210> SEQ ID NO 3
<211> LENGTH: 25
<212> TYPE: PRT
<213> ORGANISM: Homo sapiens

<400> SEQUENCE: 3

Asp Asn Arg Pro Glu Ile Trp Ile Ala Gln Glu Leu Arg Arg Ile Gly
1               5                   10                  15

Asp Glu Phe Asn Ala Tyr Tyr Ala Arg
            20                  25

<210> SEQ ID NO 4
<211> LENGTH: 25
<212> TYPE: PRT
<213> ORGANISM: Homo sapiens

<400> SEQUENCE: 4

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 5
<211> LENGTH: 25
<212> TYPE: PRT
<213> ORGANISM: Homo sapiens

<400> SEQUENCE: 5

Glu Glu Gln Trp Ala Arg Glu Ile Gly Ala Gln Leu Arg Arg Met Ala
1               5                   10                  15

Asp Asp Leu Asn Ala Gln Tyr Glu Arg
            20                  25

<210> SEQ ID NO 6
<211> LENGTH: 24
<212> TYPE: PRT
<213> ORGANISM: Homo sapiens

<400> SEQUENCE: 6

Arg Ser Ser Ala Ala Gln Leu Thr Ala Ala Arg Leu Lys Ala Leu Gly
1               5                   10                  15
```

```
Asp Glu Leu His Gln Arg Thr Met
            20

<210> SEQ ID NO 7
<211> LENGTH: 22
<212> TYPE: PRT
<213> ORGANISM: Homo sapiens

<400> SEQUENCE: 7

Ala Glu Leu Pro Pro Glu Phe Ala Ala Gln Leu Arg Lys Ile Gly Asp
1               5                   10                  15

Lys Val Tyr Cys Thr Trp
            20

<210> SEQ ID NO 8
<211> LENGTH: 25
<212> TYPE: PRT
<213> ORGANISM: Homo sapiens

<400> SEQUENCE: 8

Val Pro Ala Asp Leu Lys Asp Glu Cys Ala Gln Leu Arg Arg Ile Gly
1               5                   10                  15

Asp Lys Val Asn Leu Arg Gln Lys Leu
            20                  25

<210> SEQ ID NO 9
<211> LENGTH: 24
<212> TYPE: PRT
<213> ORGANISM: Homo sapiens

<400> SEQUENCE: 9

Gln His Arg Ala Glu Val Gln Ile Ala Arg Lys Leu Gln Cys Ile Ala
1               5                   10                  15

Asp Gln Phe His Arg Leu His Thr
            20

<210> SEQ ID NO 10
<211> LENGTH: 22
<212> TYPE: PRT
<213> ORGANISM: Homo sapiens

<400> SEQUENCE: 10

Ser Ser Ala Ala Gln Leu Thr Ala Ala Arg Leu Lys Ala Leu Gly Asp
1               5                   10                  15

Glu Leu His Gln Arg Thr
            20

<210> SEQ ID NO 11
<211> LENGTH: 25
<212> TYPE: PRT
<213> ORGANISM: Homo sapiens

<400> SEQUENCE: 11

Cys Met Glu Gly Ser Asp Ala Leu Ala Leu Arg Leu Ala Cys Ile Gly
1               5                   10                  15

Asp Glu Met Asp Val Ser Leu Arg Ala
            20                  25

<210> SEQ ID NO 12
<211> LENGTH: 24
<212> TYPE: PRT
<213> ORGANISM: Homo sapiens
```

```
<400> SEQUENCE: 12

Asp Ile Glu Arg Arg Lys Glu Val Glu Ser Ile Leu Lys Lys Asn Ser
1               5                   10                  15

Asp Trp Ile Trp Asp Trp Ser Ser
            20

<210> SEQ ID NO 13
<211> LENGTH: 22
<212> TYPE: PRT
<213> ORGANISM: Homo sapiens

<400> SEQUENCE: 13

Gly Arg Leu Ala Glu Val Cys Ala Val Leu Leu Arg Leu Gly Asp Glu
1               5                   10                  15

Leu Glu Met Ile Arg Pro
            20

<210> SEQ ID NO 14
<211> LENGTH: 25
<212> TYPE: PRT
<213> ORGANISM: Homo sapiens

<400> SEQUENCE: 14

Pro Gln Asp Ala Ser Thr Lys Lys Ser Glu Cys Leu Lys Arg Ile Gly
1               5                   10                  15

Asp Glu Leu Asp Ser Asn Met Glu Leu
            20                  25

<210> SEQ ID NO 15
<211> LENGTH: 22
<212> TYPE: PRT
<213> ORGANISM: Homo sapiens

<400> SEQUENCE: 15

Pro Ser Ser Thr Met Gly Gln Val Gly Arg Gln Leu Ala Ile Ile Gly
1               5                   10                  15

Asp Asp Ile Asn Arg Arg
            20

<210> SEQ ID NO 16
<211> LENGTH: 14
<212> TYPE: PRT
<213> ORGANISM: Homo sapiens

<400> SEQUENCE: 16

Lys Gln Ala Leu Arg Glu Ala Gly Asp Glu Phe Glu Leu Arg
1               5                   10

<210> SEQ ID NO 17
<211> LENGTH: 22
<212> TYPE: PRT
<213> ORGANISM: Homo sapiens

<400> SEQUENCE: 17

Leu Ser Pro Pro Val Val His Leu Ala Leu Ala Leu Arg Gln Ala Gly
1               5                   10                  15

Asp Asp Phe Ser Arg Arg
            20

<210> SEQ ID NO 18
<211> LENGTH: 23
<212> TYPE: PRT
```

<213> ORGANISM: Homo sapiens

<400> SEQUENCE: 18

Glu Val Ile Pro Met Ala Ala Val Lys Gln Ala Leu Arg Glu Ala Gly
1               5                   10                  15

Asp Glu Phe Glu Leu Arg Tyr
            20

<210> SEQ ID NO 19
<211> LENGTH: 20
<212> TYPE: PRT
<213> ORGANISM: Homo sapiens

<400> SEQUENCE: 19

Pro Ala Asp Pro Leu His Gln Ala Met Arg Ala Ala Gly Asp Glu Phe
1               5                   10                  15

Glu Thr Arg Phe
            20

<210> SEQ ID NO 20
<211> LENGTH: 23
<212> TYPE: PRT
<213> ORGANISM: Homo sapiens

<400> SEQUENCE: 20

Ala Thr Ser Arg Lys Leu Glu Thr Leu Arg Arg Val Gly Asp Gly Val
1               5                   10                  15

Gln Arg Asn His Glu Thr Ala
            20

<210> SEQ ID NO 21
<211> LENGTH: 19
<212> TYPE: PRT
<213> ORGANISM: Homo sapiens

<400> SEQUENCE: 21

Leu Ala Glu Val Cys Thr Val Leu Leu Arg Leu Gly Asp Glu Leu Glu
1               5                   10                  15

Gln Ile Arg

<210> SEQ ID NO 22
<211> LENGTH: 19
<212> TYPE: PRT
<213> ORGANISM: Homo sapiens

<400> SEQUENCE: 22

Met Thr Val Gly Glu Leu Ser Arg Ala Leu Gly His Glu Asn Gly Ser
1               5                   10                  15

Leu Asp Pro

<210> SEQ ID NO 23
<211> LENGTH: 22
<212> TYPE: PRT
<213> ORGANISM: Homo sapiens

<400> SEQUENCE: 23

Val Val Glu Gly Glu Lys Glu Val Glu Ala Leu Lys Lys Ser Ala Asp
1               5                   10                  15

Trp Val Ser Asp Trp Ser
            20

```
<210> SEQ ID NO 24
<211> LENGTH: 20
<212> TYPE: PRT
<213> ORGANISM: Homo sapiens

<400> SEQUENCE: 24

Ser Met Ala Arg Asp Pro Gln Arg Tyr Leu Val Ile Gln Gly Asp Asp
1               5                   10                  15

Arg Met Lys Leu
            20

<210> SEQ ID NO 25
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 25

Gln Glu Asp Ile Ile Arg Asn Ile Ala Arg His Leu Ala Xaa Val Gly
1               5                   10                  15

Asp Xaa Met Asp Arg Ser Ile Pro Pro
            20                  25

<210> SEQ ID NO 26
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 26

Asp Asn Arg Pro Glu Ile Trp Ile Ala Gln Glu Leu Arg Xaa Ile Gly
1               5                   10                  15

Asp Xaa Phe Asn Ala Tyr Tyr Ala Arg
            20                  25

<210> SEQ ID NO 27
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 27

Asn Leu Trp Ala Ala Gln Arg Tyr Gly Arg Glu Leu Arg Xaa Met Ser
1               5                   10                  15

Asp Xaa Phe Val Asp Ser Phe Lys Lys
            20                  25
```

```
<210> SEQ ID NO 28
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 28

Glu Glu Gln Trp Ala Arg Glu Ile Gly Ala Gln Leu Arg Xaa Met Ala
1               5                   10                  15

Asp Xaa Leu Asn Ala Gln Tyr Glu Arg
            20                  25

<210> SEQ ID NO 29
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 29

Arg Ser Ser Ala Ala Gln Leu Thr Ala Ala Arg Leu Lys Xaa Leu Gly
1               5                   10                  15

Asp Xaa Leu His Gln Arg Thr Met
            20

<210> SEQ ID NO 30
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: cross linked amino acid residue
<220> FEATURE:
<221> NAME/KEY: MOD_RES
<222> LOCATION: (17)..(17)
<223> OTHER INFORMATION: cross linked amino acid residue

<400> SEQUENCE: 30

Ala Glu Leu Pro Pro Glu Phe Ala Ala Gln Leu Arg Xaa Ile Gly Asp
1               5                   10                  15

Xaa Val Tyr Cys Thr Trp
            20

<210> SEQ ID NO 31
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue
```

```
<400> SEQUENCE: 31

Val Pro Ala Asp Leu Lys Asp Glu Cys Ala Gln Leu Arg Xaa Ile Gly
1               5                   10                  15

Asp Xaa Val Asn Leu Arg Gln Lys Leu
            20                  25

<210> SEQ ID NO 32
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 32

Gln His Arg Ala Glu Val Gln Ile Ala Arg Lys Leu Gln Xaa Ile Ala
1               5                   10                  15

Asp Xaa Phe His Arg Leu His Thr
            20

<210> SEQ ID NO 33
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: cross linked amino acid residue
<220> FEATURE:
<221> NAME/KEY: MOD_RES
<222> LOCATION: (17)..(17)
<223> OTHER INFORMATION: cross linked amino acid residue

<400> SEQUENCE: 33

Ser Ser Ala Ala Gln Leu Thr Ala Ala Arg Leu Lys Xaa Leu Gly Asp
1               5                   10                  15

Xaa Leu His Gln Arg Thr
            20

<210> SEQ ID NO 34
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 34

Cys Met Glu Gly Ser Asp Ala Leu Ala Leu Arg Leu Ala Xaa Ile Gly
1               5                   10                  15

Asp Xaa Met Asp Val Ser Leu Arg Ala
            20                  25

<210> SEQ ID NO 35
<211> LENGTH: 24
<212> TYPE: PRT
```

-continued

```
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 35

Asp Ile Glu Arg Arg Lys Glu Val Glu Ser Ile Leu Lys Xaa Asn Ser
1               5                   10                  15

Asp Xaa Ile Trp Asp Trp Ser Ser
            20

<210> SEQ ID NO 36
<211> LENGTH: 22
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: cross linked amino acid residue
<220> FEATURE:
<221> NAME/KEY: MOD_RES
<222> LOCATION: (16)..(16)
<223> OTHER INFORMATION: cross linked amino acid residue

<400> SEQUENCE: 36

Gly Arg Leu Ala Glu Val Cys Ala Val Leu Leu Xaa Leu Gly Asp Xaa
1               5                   10                  15

Leu Glu Met Ile Arg Pro
            20

<210> SEQ ID NO 37
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 37

Pro Gln Asp Ala Ser Thr Lys Lys Ser Glu Cys Leu Lys Xaa Ile Gly
1               5                   10                  15

Asp Xaa Leu Asp Ser Asn Met Glu Leu
            20                  25

<210> SEQ ID NO 38
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 38
```

```
Pro Ser Ser Thr Met Gly Gln Val Gly Arg Gln Leu Ala Xaa Ile Gly
1               5                   10                  15

Asp Xaa Ile Asn Arg Arg
            20
```

<210> SEQ ID NO 39
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: cross linked amino acid residue
<220> FEATURE:
<221> NAME/KEY: MOD_RES
<222> LOCATION: (10)..(10)
<223> OTHER INFORMATION: cross linked amino acid residue

<400> SEQUENCE: 39

```
Lys Gln Ala Leu Arg Xaa Ala Gly Asp Xaa Phe Glu Leu Arg
1               5                   10
```

<210> SEQ ID NO 40
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 40

```
Leu Ser Pro Pro Val Val His Leu Ala Leu Ala Leu Arg Xaa Ala Gly
1               5                   10                  15

Asp Xaa Phe Ser Arg Arg
            20
```

<210> SEQ ID NO 41
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: cross linked amino acid residue
<220> FEATURE:
<221> NAME/KEY: MOD_RES
<222> LOCATION: (18)..(18)
<223> OTHER INFORMATION: cross linked amino acid residue

<400> SEQUENCE: 41

```
Glu Val Ile Pro Met Ala Ala Val Lys Gln Ala Leu Arg Xaa Ala Gly
1               5                   10                  15

Asp Xaa Phe Glu Leu Arg Tyr
            20
```

<210> SEQ ID NO 42
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: cross linked amino acid residue
<220> FEATURE:

```
<221> NAME/KEY: MOD_RES
<222> LOCATION: (15)..(15)
<223> OTHER INFORMATION: cross linked amino acid residue

<400> SEQUENCE: 42

Pro Ala Asp Pro Leu His Gln Ala Met Arg Xaa Ala Gly Asp Xaa Phe
1               5                   10                  15

Glu Thr Arg Phe
            20

<210> SEQ ID NO 43
<211> LENGTH: 23
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: cross linked amino acid residue
<220> FEATURE:
<221> NAME/KEY: MOD_RES
<222> LOCATION: (15)..(15)
<223> OTHER INFORMATION: cross linked amino acid residue

<400> SEQUENCE: 43

Ala Thr Ser Arg Lys Leu Glu Thr Leu Arg Xaa Val Gly Asp Xaa Val
1               5                   10                  15

Gln Arg Asn His Glu Thr Ala
            20

<210> SEQ ID NO 44
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: cross linked amino acid residue
<220> FEATURE:
<221> NAME/KEY: MOD_RES
<222> LOCATION: (14)..(14)
<223> OTHER INFORMATION: cross linked amino acid residue

<400> SEQUENCE: 44

Leu Ala Glu Val Cys Thr Val Leu Leu Xaa Leu Gly Asp Xaa Leu Glu
1               5                   10                  15

Gln Ile Arg

<210> SEQ ID NO 45
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: cross linked amino acid residue
<220> FEATURE:
<221> NAME/KEY: MOD_RES
<222> LOCATION: (16)..(16)
<223> OTHER INFORMATION: cross linked amino acid residue

<400> SEQUENCE: 45

Met Thr Val Gly Glu Leu Ser Arg Ala Leu Gly Xaa Glu Asn Gly Xaa
1               5                   10                  15

Leu Asp Pro

<210> SEQ ID NO 46
<211> LENGTH: 22
```

```
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: cross linked amino acid residue
<220> FEATURE:
<221> NAME/KEY: MOD_RES
<222> LOCATION: (17)..(17)
<223> OTHER INFORMATION: cross linked amino acid residue

<400> SEQUENCE: 46

Val Val Glu Gly Glu Lys Glu Val Glu Ala Leu Lys Xaa Ser Ala Asp
1               5                   10                  15

Xaa Val Ser Asp Trp Ser
            20

<210> SEQ ID NO 47
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: cross linked amino acid residue
<220> FEATURE:
<221> NAME/KEY: MOD_RES
<222> LOCATION: (16)..(16)
<223> OTHER INFORMATION: cross linked amino acid residue

<400> SEQUENCE: 47

Ser Met Ala Arg Asp Pro Gln Arg Tyr Leu Val Xaa Gln Gly Asp Xaa
1               5                   10                  15

Arg Met Lys Leu
            20

<210> SEQ ID NO 48
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 48

Gln Glu Asp Ile Ile Arg Asn Ile Xaa Arg His Leu Xaa Gln Val Gly
1               5                   10                  15

Asp Ser Met Asp Arg Ser Ile Pro Pro
            20                  25

<210> SEQ ID NO 49
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 49
```

-continued

```
Asp Asn Arg Pro Glu Ile Trp Ile Xaa Gln Glu Leu Xaa Arg Ile Gly
1               5                   10                  15

Asp Glu Phe Asn Ala Tyr Tyr Ala Arg
            20                  25

<210> SEQ ID NO 50
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 50

Asn Leu Trp Ala Ala Gln Arg Tyr Xaa Arg Glu Leu Xaa Arg Met Ser
1               5                   10                  15

Asp Glu Phe Val Asp Ser Phe Lys Lys
            20                  25

<210> SEQ ID NO 51
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 51

Glu Glu Gln Trp Ala Arg Glu Ile Xaa Ala Gln Leu Xaa Arg Met Ala
1               5                   10                  15

Asp Asp Leu Asn Ala Gln Tyr Glu Arg
            20                  25

<210> SEQ ID NO 52
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 52

Arg Ser Ser Ala Ala Gln Leu Thr Xaa Ala Arg Leu Xaa Ala Leu Gly
1               5                   10                  15

Asp Glu Leu His Gln Arg Thr Met
            20

<210> SEQ ID NO 53
<211> LENGTH: 22
<212> TYPE: PRT
<213> ORGANISM: Homo sapiens
<220> FEATURE:
<221> NAME/KEY: MOD_RES
```

```
<222> LOCATION: (8)..(8)
<223> OTHER INFORMATION: cross linked amino acid residue
<220> FEATURE:
<221> NAME/KEY: MOD_RES
<222> LOCATION: (12)..(12)
<223> OTHER INFORMATION: cross linked amino acid residue

<400> SEQUENCE: 53

Ala Glu Leu Pro Pro Glu Phe Xaa Ala Gln Leu Xaa Lys Ile Gly Asp
1               5                   10                  15

Lys Val Tyr Cys Thr Trp
            20

<210> SEQ ID NO 54
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 54

Val Pro Ala Asp Leu Lys Asp Glu Xaa Ala Gln Leu Xaa Arg Ile Gly
1               5                   10                  15

Asp Lys Val Asn Leu Arg Gln Lys Leu
            20                  25

<210> SEQ ID NO 55
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 55

Gln His Arg Ala Glu Val Gln Ile Xaa Arg Lys Leu Xaa Cys Ile Ala
1               5                   10                  15

Asp Gln Phe His Arg Leu His Thr
            20

<210> SEQ ID NO 56
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: cross linked amino acid residue
<220> FEATURE:
<221> NAME/KEY: MOD_RES
<222> LOCATION: (12)..(12)
<223> OTHER INFORMATION: cross linked amino acid residue

<400> SEQUENCE: 56

Ser Ser Ala Ala Gln Leu Thr Xaa Ala Arg Leu Xaa Ala Leu Gly Asp
1               5                   10                  15
```

Glu Leu His Gln Arg Thr
            20

<210> SEQ ID NO 57
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 57

Cys Met Glu Gly Ser Asp Ala Leu Xaa Leu Arg Leu Xaa Cys Ile Gly
1               5                   10                  15

Asp Glu Met Asp Val Ser Leu Arg Ala
            20                  25

<210> SEQ ID NO 58
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 58

Asp Ile Glu Arg Arg Lys Glu Val Xaa Ser Ile Leu Xaa Lys Asn Ser
1               5                   10                  15

Asp Trp Ile Trp Asp Trp Ser Ser
            20

<210> SEQ ID NO 59
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (11)..(11)
<223> OTHER INFORMATION: cross linked amino acid residue

<400> SEQUENCE: 59

Gly Arg Leu Ala Glu Val Xaa Ala Val Leu Xaa Arg Leu Gly Asp Glu
1               5                   10                  15

Leu Glu Met Ile Arg Pro
            20

<210> SEQ ID NO 60
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:

```
<221> NAME/KEY: MOD_RES
<222> LOCATION: (13)..(13)
<223> OTHER INFORMATION: cross linked amino acid residue

<400> SEQUENCE: 60

Pro Gln Asp Ala Ser Thr Lys Lys Xaa Glu Cys Leu Xaa Arg Ile Gly
1               5                   10                  15

Asp Glu Leu Asp Ser Asn Met Glu Leu
            20                  25

<210> SEQ ID NO 61
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 61

Pro Ser Ser Thr Met Gly Gln Val Xaa Arg Gln Leu Xaa Ile Ile Gly
1               5                   10                  15

Asp Asp Ile Asn Arg Arg
            20

<210> SEQ ID NO 62
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: cross linked amino acid residue
<220> FEATURE:
<221> NAME/KEY: MOD_RES
<222> LOCATION: (5)..(5)
<223> OTHER INFORMATION: cross linked amino acid residue

<400> SEQUENCE: 62

Xaa Gln Ala Leu Xaa Glu Ala Gly Asp Glu Phe Glu Leu Arg
1               5                   10

<210> SEQ ID NO 63
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 63

Leu Ser Pro Pro Val Val His Leu Xaa Leu Ala Leu Xaa Gln Ala Gly
1               5                   10                  15

Asp Asp Phe Ser Arg Arg
            20

<210> SEQ ID NO 64
<211> LENGTH: 23
<212> TYPE: PRT
```

-continued

```
<213> ORGANISM: Homo sapiens
<220> FEATURE:
<221> NAME/KEY: MOD_RES
<222> LOCATION: (9)..(9)
<223> OTHER INFORMATION: cross linked amino acid residue
<220> FEATURE:
<221> NAME/KEY: MOD_RES
<222> LOCATION: (13)..(13)
<223> OTHER INFORMATION: cross linked amino acid residue

<400> SEQUENCE: 64

Glu Val Ile Pro Met Ala Ala Val Xaa Gln Ala Leu Xaa Glu Ala Gly
1               5                   10                  15

Asp Glu Phe Glu Leu Arg Tyr
            20

<210> SEQ ID NO 65
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: cross linked amino acid residue
<220> FEATURE:
<221> NAME/KEY: MOD_RES
<222> LOCATION: (10)..(10)
<223> OTHER INFORMATION: cross linked amino acid residue

<400> SEQUENCE: 65

Pro Ala Asp Pro Leu Xaa Gln Ala Met Xaa Ala Ala Gly Asp Glu Phe
1               5                   10                  15

Glu Thr Arg Phe
            20

<210> SEQ ID NO 66
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: cross linked amino acid residue
<220> FEATURE:
<221> NAME/KEY: MOD_RES
<222> LOCATION: (10)..(10)
<223> OTHER INFORMATION: cross linked amino acid residue

<400> SEQUENCE: 66

Ala Thr Ser Arg Lys Xaa Glu Thr Leu Xaa Arg Val Gly Asp Gly Val
1               5                   10                  15

Gln Arg Asn His Glu Thr Ala
            20

<210> SEQ ID NO 67
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: cross linked amino acid residue
<220> FEATURE:
<221> NAME/KEY: MOD_RES
<222> LOCATION: (9)..(9)
<223> OTHER INFORMATION: cross linked amino acid residue

<400> SEQUENCE: 67
```

```
Leu Ala Glu Val Xaa Thr Val Leu Xaa Arg Leu Gly Asp Glu Leu Glu
1               5                   10                  15

Gln Ile Arg

<210> SEQ ID NO 68
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (11)..(11)
<223> OTHER INFORMATION: cross linked amino acid residue

<400> SEQUENCE: 68

Met Thr Val Gly Glu Leu Xaa Arg Ala Leu Xaa His Glu Asn Gly Ser
1               5                   10                  15

Leu Asp Pro

<210> SEQ ID NO 69
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: cross linked amino acid residue
<220> FEATURE:
<221> NAME/KEY: MOD_RES
<222> LOCATION: (12)..(12)
<223> OTHER INFORMATION: cross linked amino acid residue

<400> SEQUENCE: 69

Val Val Glu Gly Glu Lys Glu Xaa Gly Ala Leu Xaa Lys Ser Ala Asp
1               5                   10                  15

Trp Val Ser Asp Trp Ser
            20

<210> SEQ ID NO 70
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (11)..(11)
<223> OTHER INFORMATION: cross linked amino acid residue

<400> SEQUENCE: 70

Ser Met Ala Arg Asp Pro Xaa Arg Tyr Leu Xaa Ile Gln Gly Asp Asp
1               5                   10                  15

Arg Met Lys Leu
            20

<210> SEQ ID NO 71
<211> LENGTH: 16
<212> TYPE: PRT
<213> ORGANISM: Homo sapiens

<400> SEQUENCE: 71
```

```
Leu Ser Gln Glu Thr Phe Ser Asp Leu Trp Lys Leu Leu Pro Glu Asn
1               5                   10                  15

<210> SEQ ID NO 72
<211> LENGTH: 19
<212> TYPE: PRT
<213> ORGANISM: Homo sapiens

<400> SEQUENCE: 72

Pro Pro Leu Ser Gln Glu Thr Phe Ser Asp Leu Trp Lys Leu Leu Pro
1               5                   10                  15

Glu Asn Asn

<210> SEQ ID NO 73
<211> LENGTH: 19
<212> TYPE: PRT
<213> ORGANISM: Homo sapiens

<400> SEQUENCE: 73

Pro Pro Leu Ser Gln Glu Thr Phe Ser Asp Leu Trp Lys Leu Leu Ser
1               5                   10                  15

Glu Asn Asn

<210> SEQ ID NO 74
<211> LENGTH: 30
<212> TYPE: PRT
<213> ORGANISM: Homo sapiens

<400> SEQUENCE: 74

Asp Pro Ser Val Glu Pro Pro Leu Ser Gln Glu Thr Phe Ser Asp Leu
1               5                   10                  15

Trp Lys Leu Leu Pro Glu Asn Asn Val Leu Ser Pro Leu Pro
            20                  25                  30

<210> SEQ ID NO 75
<211> LENGTH: 30
<212> TYPE: PRT
<213> ORGANISM: Homo sapiens

<400> SEQUENCE: 75

Asp Pro Ser Val Glu Pro Pro Leu Ser Gln Glu Thr Phe Ser Asp Leu
1               5                   10                  15

Trp Lys Leu Leu Ser Glu Asn Asn Val Leu Ser Pro Leu Pro
            20                  25                  30

<210> SEQ ID NO 76
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: cross linked amino acid residue
<220> FEATURE:
<221> NAME/KEY: MOD_RES
<222> LOCATION: (5)..(5)
<223> OTHER INFORMATION: cross linked amino acid residue

<400> SEQUENCE: 76

Xaa Ser Gln Glu Xaa Phe Ser Asp Leu Trp Lys Leu Leu Pro Glu Asn
1               5                   10                  15

<210> SEQ ID NO 77
```

```
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: cross linked amino acid residue
<220> FEATURE:
<221> NAME/KEY: MOD_RES
<222> LOCATION: (7)..(7)
<223> OTHER INFORMATION: cross linked amino acid residue

<400> SEQUENCE: 77

Pro Pro Xaa Ser Gln Glu Xaa Phe Ser Asp Leu Trp Lys Leu Leu Pro
1               5                   10                  15

Glu Asn Asn

<210> SEQ ID NO 78
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: cross linked amino acid residue
<220> FEATURE:
<221> NAME/KEY: MOD_RES
<222> LOCATION: (7)..(7)
<223> OTHER INFORMATION: cross linked amino acid residue

<400> SEQUENCE: 78

Pro Pro Xaa Ser Gln Glu Xaa Phe Ser Asp Leu Trp Lys Leu Leu Ser
1               5                   10                  15

Glu Asn Asn

<210> SEQ ID NO 79
<211> LENGTH: 30
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: cross linked amino acid residue
<220> FEATURE:
<221> NAME/KEY: MOD_RES
<222> LOCATION: (12)..(12)
<223> OTHER INFORMATION: cross linked amino acid residue

<400> SEQUENCE: 79

Asp Pro Ser Val Glu Pro Pro Xaa Ser Gln Glu Xaa Phe Ser Asp Leu
1               5                   10                  15

Trp Lys Leu Leu Pro Glu Asn Asn Val Leu Ser Pro Leu Pro
            20                  25                  30

<210> SEQ ID NO 80
<211> LENGTH: 30
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: cross linked amino acid residue
<220> FEATURE:
<221> NAME/KEY: MOD_RES
<222> LOCATION: (12)..(12)
<223> OTHER INFORMATION: cross linked amino acid residue

<400> SEQUENCE: 80
```

```
Asp Pro Ser Val Glu Pro Pro Xaa Ser Gln Glu Xaa Phe Ser Asp Leu
1               5                   10                  15

Trp Lys Leu Leu Ser Glu Asn Asn Val Leu Ser Pro Leu Pro
            20                  25                  30
```

<210> SEQ ID NO 81
<211> LENGTH: 16
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: cross linked amino acid residue
<220> FEATURE:
<221> NAME/KEY: MOD_RES
<222> LOCATION: (15)..(15)
<223> OTHER INFORMATION: cross linked amino acid residue

<400> SEQUENCE: 81

```
Leu Ser Gln Glu Thr Phe Ser Asp Leu Trp Xaa Leu Leu Pro Xaa Asn
1               5                   10                  15
```

<210> SEQ ID NO 82
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: cross linked amino acid residue
<220> FEATURE:
<221> NAME/KEY: MOD_RES
<222> LOCATION: (17)..(17)
<223> OTHER INFORMATION: cross linked amino acid residue

<400> SEQUENCE: 82

```
Pro Pro Leu Ser Gln Glu Thr Phe Ser Asp Leu Trp Xaa Leu Leu Pro
1               5                   10                  15

Xaa Asn Asn
```

<210> SEQ ID NO 83
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: cross linked amino acid residue
<220> FEATURE:
<221> NAME/KEY: MOD_RES
<222> LOCATION: (17)..(17)
<223> OTHER INFORMATION: cross linked amino acid residue

<400> SEQUENCE: 83

```
Pro Pro Leu Ser Gln Glu Thr Phe Ser Asp Leu Trp Xaa Leu Leu Ser
1               5                   10                  15

Xaa Asn Asn
```

<210> SEQ ID NO 84
<211> LENGTH: 30
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: cross linked amino acid residue
<220> FEATURE:
<221> NAME/KEY: MOD_RES
<222> LOCATION: (22)..(22)

```
<223> OTHER INFORMATION: cross linked amino acid residue

<400> SEQUENCE: 84

Asp Pro Ser Val Glu Pro Pro Leu Ser Gln Glu Thr Phe Ser Asp Leu
1               5                   10                  15

Trp Xaa Leu Leu Pro Xaa Asn Asn Val Leu Ser Pro Leu Pro
            20                  25                  30

<210> SEQ ID NO 85
<211> LENGTH: 30
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: cross linked amino acid residue
<220> FEATURE:
<221> NAME/KEY: MOD_RES
<222> LOCATION: (22)..(22)
<223> OTHER INFORMATION: cross linked amino acid residue

<400> SEQUENCE: 85

Asp Pro Ser Val Glu Pro Pro Leu Ser Gln Glu Thr Phe Ser Asp Leu
1               5                   10                  15

Trp Xaa Leu Leu Ser Xaa Asn Asn Val Leu Ser Pro Leu Pro
            20                  25                  30

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 86

Asp Arg Val Tyr Ile His Pro Phe
1               5

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 87

Glu Gln Arg Leu Gly Asn Gln Trp Ala Val Gly His Leu Met
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 88

Arg Pro Pro Gly Phe Ser Pro Phe Arg
1               5

<210> SEQ ID NO 89
<211> LENGTH: 10
<212> TYPE: PRT
<213> ORGANISM: Artificial Sequence
```

```
<220> FEATURE:
<223> OTHER INFORMATION: Description of Artificial Sequence:
      Synthetic peptide

<400> SEQUENCE: 89

Ile Ser His Lys Asp Met Gln Leu Gly Arg
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 90

Ala Arg Ala Ser His Leu Gly Leu Ala Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 91

Ser Tyr Ser Met Glu His Phe Arg Trp Gly Lys Pro Val
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (3)..(3)
<223> OTHER INFORMATION: cross linked amino acid residue
<220> FEATURE:
<221> NAME/KEY: MOD_RES
<222> LOCATION: (5)..(5)
<223> OTHER INFORMATION: cross linked amino acid residue

<400> SEQUENCE: 92

Asp Arg Xaa Tyr Xaa His Pro Phe
1               5

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (14)..(14)
<223> OTHER INFORMATION: cross linked amino acid residue

<400> SEQUENCE: 93
```

```
Glu Gln Arg Leu Gly Asn Xaa Trp Ala Val Gly His Leu Xaa
1               5                   10
```

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (4)..(4)
<223> OTHER INFORMATION: cross linked amino acid residue
<220> FEATURE:
<221> NAME/KEY: MOD_RES
<222> LOCATION: (10)..(10)
<223> OTHER INFORMATION: cross linked amino acid residue

<400> SEQUENCE: 94

```
Arg Pro Pro Xaa Phe Ser Pro Phe Arg Xaa
1               5                   10
```

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (11)..(11)
<223> OTHER INFORMATION: cross linked amino acid residue

<400> SEQUENCE: 95

```
Ile Ser His Lys Asp Met Xaa Leu Gly Arg Xaa
1               5                   10
```

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (7)..(7)
<223> OTHER INFORMATION: cross linked amino acid residue
<220> FEATURE:
<221> NAME/KEY: MOD_RES
<222> LOCATION: (11)..(11)
<223> OTHER INFORMATION: cross linked amino acid residue

<400> SEQUENCE: 96

```
Ala Arg Ala Ser His Leu Xaa Leu Ala Arg Xaa
1               5                   10
```

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES

```
<222> LOCATION: (5)..(5)
<223> OTHER INFORMATION: cross linked amino acid residue
<220> FEATURE:
<221> NAME/KEY: MOD_RES
<222> LOCATION: (10)..(10)
<223> OTHER INFORMATION: cross linked amino acid residue

<400> SEQUENCE: 97

Ser Tyr Ser Met Xaa His Phe Arg Trp Xaa Lys Pro Val
1               5                   10

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 98

Asp Ile Ile Arg Asn Ile Ala Arg His Leu Ala Gln Val Gly Asp Ser
1               5                   10                  15

Met Asp Arg Ser Ile
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (17)..(17)
<223> OTHER INFORMATION: norleucine
<220> FEATURE:
<223> OTHER INFORMATION: crosslink between residues at positions 12
      and 16

<400> SEQUENCE: 99

Asp Ile Ile Arg Asn Ile Ala Arg His Leu Ala Cys Val Gly Asp Cys
1               5                   10                  15

Xaa Asp Arg Ser Ile
            20

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: norleucine

<400> SEQUENCE: 100

Asp Ile Ile Ala Arg His Leu Ala Cys Val Gly Asp Cys Xaa Asp Arg
1               5                   10                  15

Ser Ile
```

BIS-SULFHYDRYL MACROCYCLIZATION SYSTEMS

CROSS-REFERENCE

This application is a continuation application of U.S. application Ser. No. 12/690,076, filed Jan. 19, 2010, now U.S. Pat. No. 8,609,809, which is a continuation application of U.S. application Ser. No. 11/957,325, filed Dec. 14, 2007, now U.S. Pat. No. 7,960,506, which claims benefit to U.S. Provisional Application Serial No. 60/874,819, filed Dec. 14, 2006, all of which is incorporated herein by reference in its entirety and to which application we claim priority under 35 USC §120.

BACKGROUND OF THE INVENTION

Peptides are becoming increasingly important in drug discovery. Unmodified peptides often suffer from poor metabolic stability, poor cell penetrability, and promiscuous binding due to conformational flexibility. To improve these properties, researchers have generated cyclic peptides and peptidomimetics by a variety of methods, including disulfide bond formation, amide bond formation, and carbon-carbon bond formation (Jackson et al. (1991), *J. Am. Chem. Soc.* 113:9391-9392; Phelan et al. (1997), *J. Am. Chem. Soc.* 119: 455-460; Taylor (2002), *Biopolymers* 66: 49-75; Brunel et al. (2005), *Chem. Commun.* (20):2552-2554; Hiroshige et al. (1995), *J. Am. Chem. Soc.* 117: 11590-11591; Blackwell et al. (1998), *Angew. Chem. Int. Ed.* 37:3281-3284; Schafmeister et al. (2000), *J. Am. Chem. Soc.* 122:5891-5892). Limitations of these methods include poor metabolic stability (disulfide and amide bonds), poor cell penetrability (disulfide and amide bonds), and the use of potentially toxic metals (carbon-carbon bonds).

SUMMARY OF THE INVENTION

The present invention provides novel peptidomimetic macrocycles and methods for their preparation and use. In general, the synthesis of these peptidomimetic macrocycles involves (1) synthesizing a precursor peptide containing two free —SH moieties; and (2) contacting the precursor peptide with a bis-alkylating reagent to yield a novel peptidomimetic macrocycle. This general method permits the covalent linkage of at least two free thiolate moieties in a precursor peptide to yield novel compounds that exhibit improved biological properties such as structural stability, affinity for a target, resistance to proteolytic degradation and cell penetrance. In addition, this general method permits the rapid and selective incorporation of a broad diversity of moieties into the peptidomimetic macrocycle to permit the generation of a library of related macrocycles. This general method also permits the facile incorporation of labels (e.g., radioisotopes, chemiluminescent or fluorescent labels) or therapeutic agents.

Thus, in one aspect, the invention provides a peptidomimetic macrocycle of Formula (I):

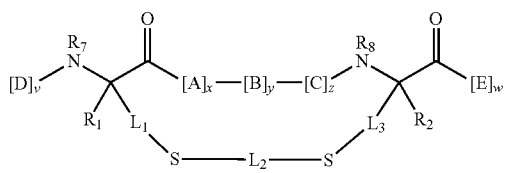

(Formula I)

wherein:
each A, C, D, and E is independently a natural or non-natural amino acid;
B is a natural or non-natural amino acid, amino acid analog,

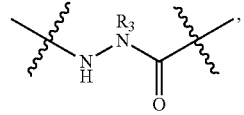

[—NH-$L_4$-CO—], [—NH-$L_4$-$SO_2$—], or [—NH-$L_4$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;
$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, unsubstituted or substituted with $R_5$;
$L_1$, $L_2$, $L_3$ and $L_4$ are independently alkylene, alkenylene, alkynylene, heteroalkylene, cycloalkylene, heterocycloalkylene, cycloarylene, heterocycloarylene or [—$R_4$—K—$R_4$-]n, each being unsubstituted or substituted with $R_5$;
K is O, S, SO, $SO_2$, CO, $CO_2$, or $CONR_3$;
each $R_4$ is alkylene, alkenylene, alkynylene, heteroalkylene, cycloalkylene, heterocycloalkylene, arylene, or heteroarylene;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
$R_7$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with a D residue;
$R_8$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with an E residue;
v is an integer from 1-1000;
w is an integer from 1-1000;
x is an integer from 0-10;
y is an integer from 0-10;
z is an integer from 0-10;
n is an integer from 1-5; and
x+y+z is at least 3.

In some embodiments the peptidomimetic macrocycle comprises an α-helix and $R_8$ is —H. In some embodiments, at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-. Alternatively, both $R_1$ and $R_2$ are independently alkyl, alkenyl, alkynyl, arylalkyl, cycloalkyl, cycloalkylalkyl, heteroalkyl, or heterocycloalkyl, unsubstituted or substituted with halo-. In other embodiments, at least one of $R_1$ and $R_2$ is alkyl, unsubstituted or substituted with halo-, or both $R_1$ and $R_2$ are independently alkyl, unsubstituted or substituted with halo-. In yet other embodiments, at least one of $R_1$ and $R_2$ is methyl, or both $R_1$ and $R_2$ are methyl.

In some embodiments, at least one of D and E is a natural or unnatural amino acid substituted with a high molecular weight lipid or hydrocarbon. In other embodiments, at least one of D and E is attached to an additional macrocycle-forming linker of the formula [-$L_1$-S-$L_2$-S-$L_3$-].

In some cases, a secondary structure of the peptidomimetic macrocycle is more stable than a corresponding secondary structure of a corresponding non-macrocyclic polypeptide. In some embodiments, the peptidomimetic macrocycle of the invention also comprises an α-helix. Such an α-helix, for example, comprises from 1 turn to 5 turns. Such an α-helix is, for example, more stable than an α-helix of a corresponding non-macrocyclic polypeptide. In some embodiments, [-L$_1$-S-L$_2$-S-L$_3$-] spans from 1 turn to 5 turns of the α-helix, such as approximately 1, 2, 3, 4 or 5 turns of the α-helix. For example, [-L$_1$-S-L$_2$-S-L$_3$-] spans approximately 1 turn of the α-helix. Exemplary lengths of [-L$_1$-S-L$_2$-S-L$_3$-] are about 5 Å to about 9 Å per turn of the α-helix. In some embodiments, the length of [-L$_1$-S-L$_2$-S-L$_3$-] is approximately equal to the length of from about 5 carbon-carbon bonds to about 13 carbon-carbon bonds, or from about 7 carbon-carbon bonds to about 10 carbon-carbon bonds. In other embodiments, the macrocycle of the invention comprises a ring of about 17 atoms to 25 atoms.

In yet other embodiments, the peptidomimetic macrocycle of the invention comprises an α-helix which comprises about 2 turns. For example, the length of [-L$_1$-S-L$_2$-S-L$_3$-] is approximately equal to the length of from about 8 carbon-carbon bonds to about 16 carbon-carbon bonds, or from about 10 carbon-carbon bonds to about 13 carbon-carbon bonds. In other embodiments, the macrocycle of the invention comprises a ring of about 29 atoms to about 37 atoms.

The present invention also provides a compound of Formula IIa:

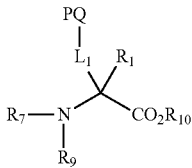

(Formula IIa)

wherein:
R$_1$ is alkyl, alkenyl, alkynyl, arylalkyl, cycloalkyl, cycloalkylalkyl, heteroalkyl, or heterocycloalkyl;
L$_1$ is independently alkylene, alkenylene, alkynylene, heteroalkylene, cycloalkylene, heterocycloalkylene, cycloarylene, heterocycloarylene or [—R$_4$—K—R$_4$-]n, unsubstituted or substituted with R$_5$;
K is O, S, SO, SO$_2$, CO, CO$_2$, or CONR$_3$;
R$_4$ is alkylene, alkenylene, alkynylene, heteroalkylene, cycloalkylene, heterocycloalkylene, arylene, or heteroarylene;
R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;
R$_6$ is independently —H, alkyl, alkenyl, alkynyl, arylalkyl, cycloalkylalkyl, heteroalkylalkyl, heterocyclyalkyl, a fluorescent moiety, a radioisotope or a therapeutic agent;
R$_7$ is —H, alkyl, alkenyl, alkynyl, arylalkyl, cycloalkylalkyl, heteroalkylalkyl, or heterocyclyalkyl;
R$_9$ and R$_{10}$ are independently —H or a protecting group suitable for peptide synthesis;
n is an integer from 1 to 5;
Q is S; and
P is —H, -trityl, p-methoxytrityl, —S t-butyl, or any other protecting group suitable for peptide synthesis; or Q and P when taken together form a moiety capable of undergoing chemical transformation into an —SH group.

In some embodiments, R$_1$ is alkyl, unsubstituted or substituted with halo-. In other embodiments, R$_1$ is unsubstituted alkyl. In yet other embodiments, R$_1$ is methyl. In still other embodiments, at least one of R$_9$ and R$_{10}$ is a protected group suitable for peptide synthesis.

The present invention also provides a kit comprising a) a compound of Formulas IIa and a compound of Formula IIb:

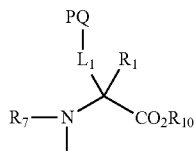

(Formula IIa)

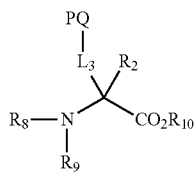

(Formula IIb)

wherein:
R$_1$ is alkyl, alkenyl, alkynyl, arylalkyl, cycloalkyl, heteroalkyl, or heterocycloalkyl, unsubstituted or substituted with halo-;
R$_2$ is —H, alkyl, alkenyl, alkynyl, arylalkyl, cycloalkyl, heteroalkyl, or heterocycloalkyl, unsubstituted or substituted with halo-;
L$_1$ and L$_3$ are independently alkylene, alkenylene, alkynylene, heteroalkylene, cycloalkylene, heterocycloalkylene, cycloarylene, or heterocycloarylene or [—R$_4$—K—R$_4$-]n, each being unsubstituted or substituted with R$_5$;
K is O, S, SO, SO$_2$, CO, CO$_2$, or CONR$_3$;
R$_4$ is alkylene, alkenylene, alkynylene, heteroalkylene, cycloalkylene, heterocycloalkylene, arylene, or heteroarylene;
each R$_5$ is independently halogen, alkyl, —OR$_6$, —N(R$_6$)$_2$, —SR$_6$, —SOR$_6$, —SO$_2$R$_6$, —CO$_2$R$_6$, —R$_6$, a fluorescent moiety, a radioisotope, or a therapeutic agent;
each R$_6$ is independently —H, alkyl, alkenyl, alkynyl, arylalkyl, cycloalkylalkyl, heteroalkylalkyl, heterocyclyalkyl, a fluorescent moiety, a radioisotope, or a therapeutic agent;
R$_7$ and R$_8$ are independently —H, alkyl, alkenyl, alkynyl, arylalkyl, cycloalkylalkyl, heteroalkylalkyl, or heterocyclyalkyl;
R$_9$ and R$_{10}$ are each independently —H or any protecting group suitable for liquid or solid phase peptide synthesis;
Q is S;
P is —H, -trityl, p-methoxytrityl, —S t-butyl, or any other protecting group suitable for liquid or solid phase peptide synthesis; or Q and P when taken together form a moiety capable of undergoing chemical transformation into an —SH group; n is an integer from 1 to 5;
and b) a macrocycle-forming linker of the structure:

wherein L$_2$ is alkylene, alkenylene, alkynylene, heteroalkylene, cycloalkylene, heterocycloalkylene, cycloarylene, heterocycloarylene, or [—R$_{11}$—K—R$_{11}$-]n, each being unsubstituted or substituted with R$_{12}$;
each R$_{11}$ is alkylene, alkenylene, alkynylene, heteroalkylene, cycloalkylene, heterocycloalkylene, arylene, or heteroarylene;

each $R_{12}$ is independently halogen, alkyl, —$OR_D$, —$N(R_6)_{13}$, —$SR_{13}$, —$SOR_{13}$, —$SO_2R_{13}$, —$CO_2R_{13}$, —$R_{13}$, a fluorescent moiety, a radioisotope, or a therapeutic agent;

each $R_{13}$ is independently —H, alkyl, alkenyl, alkynyl, arylalkyl, cycloalkylalkyl, heteroalkylalkyl, heterocyclyalkyl, a fluorescent moiety, a radioisotope, or a therapeutic agent; and X and Y are each independently a reactive group capable of reacting with a thiol group.

In some embodiments, $R_2$ is alkyl, alkenyl, alkynyl, arylalkyl, cycloalkyl, heteroalkyl, or heterocycloalkyl, unsubstituted or substituted with halo. In specific such embodiments, $R_1$ and $R_2$ are alkyl. For example, $R_1$ and $R_2$ are methyl or trifluoromethyl.

A method for synthesizing a peptidomimetic macrocycle, the method comprising the step of contacting a peptidomimetic precursor of the Formula III:

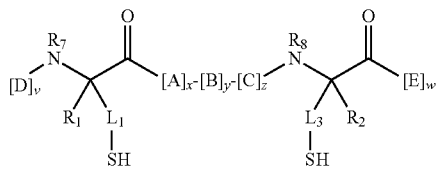

(Formula III)

with a compound formula X-$L_2$-Y, wherein v, w, x, y, z, A, B, C, D, E, $R_1$, $R_2$, $R_7$, $R_8$, $L_1$, $L_2$, and $L_3$ are as defined for the compound of formula I; and X and Y are each independently a reactive group capable of reacting with a thiol group;

x+y+z is at least 3;

and further wherein said contacting step results in a covalent linkage being formed between the two thiol groups in Formula III.

In some embodiments, performing a method of the invention results in the formation of a peptidomimetic macrocycle of Formula (I) as described herein.

In certain embodiments, at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-. Alternatively, both $R_1$ and $R_2$ are independently alkyl, alkenyl, alkynyl, arylalkyl, cycloalkyl, cycloalkylalkyl, heteroalkyl, or heterocycloalkyl, unsubstituted or substituted with halo-. In other embodiments, at least one of $R_1$ and $R_2$ is alkyl, unsubstituted or substituted with halo-, or both $R_1$ and $R_2$ are independently alkyl, unsubstituted or substituted with halo-. In yet other embodiments, at least one of $R_1$ and $R_2$ is methyl, or both $R_1$ and $R_2$ are methyl.

In some embodiments, the peptidomimetic precursor is expressed in cells. The peptidomimetic precursor is also purified, in some embodiments, prior to the contacting step. The obtained peptidomimetic macrocycle is, in some instances, purified after the contacting step, and/or refolded after the contacting step.

The described method is, for example, performed in solution, or it performed on a solid support. The contacting step is, in some cases, performed in the presence of a target macromolecule that binds to the peptidomimetic precursor under conditions that favor said binding, or it is performed in the presence of a target macromolecule that binds preferentially to the peptidomimetic precursor under conditions that favor said binding. In some embodiments, the described method is applied to synthesize a library of peptidomimetic macrocycles.

In some embodiments, a peptidomimetic macrocycle prepared by the method of the invention comprises an α-helix in aqueous solution. In other embodiments, the peptidomimetic macrocycle exhibits increased α-helical structure in aqueous solution compared to a corresponding non-macrocyclic polypeptide. In still other embodiments, the peptidomimetic macrocycle exhibits increased thermal stability, increased biological activity, increased resistance to proteolytic degradation, or increased ability to penetrate living cells compared to a corresponding non-macrocyclic polypeptide. In some embodiments, the two thiol moieties of the compound of Formula III are sidechains of an amino acid selected from the group consisting of L-cysteine, D-cysteine, α-methyl L-cysteine, and α-methyl D-cysteine. In certain embodiments of the method of the invention, x+y+z is 3, and A, B and C are independently natural or non-natural amino acids.

The method described is, for example, performed in a solvent selected from the group consisting of protic solvent, aqueous solvent, organic solvent, and mixtures thereof. In some embodiments, the solvent is DMF, dichloroethane, $NH_3$, $NH_3$/MeOH, $NH_3$/DMF, or aqueous guanidinium-HCL. In some embodiments, the solvent is also be a solvent that favors helix formation, such as water.

In some embodiments of the compounds and methods described herein, $L_2$ is an alkyl group. In other embodiments, X and Y are independently chosen halogen groups such as Cl—, Br— or I—.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows a MALDI spectrum of a peptidomimetic macrocycle of the invention.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

As used herein, the term "macrocycle" refers to a molecule having a chemical structure including a ring or cycle formed by at least 9 covalently bonded atoms.

As used herein, the term "peptidomimetic macrocycle" refers to a compound comprising a plurality of amino acid residues joined by a plurality of peptide bonds and at least one macrocycle-forming linker which forms a macrocycle between the α carbon of one naturally-occurring amino acid residue or non-naturally-occurring amino acid residue or amino acid analog residue and the α carbon of another naturally-occurring amino acid residue or non-naturally-occurring amino acid residue or amino acid analog residue. The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle.

As used herein, the term "stability" refers to the maintenance of a defined secondary structure in solution by a peptide or peptidomimetic macrocycle of the invention as measured by circular dichroism, NMR or another biophysical measure, or resistance to proteolytic degradation in vitro or in vivo. Non-limiting examples of secondary structures contemplated in this invention are $\alpha$-helices, $\beta$-turns, and $\beta$-pleated sheets.

As used herein, the term "helical stability" refers to the maintenance of a helical structure by a peptide or peptidomimetic macrocycle of the invention as measured by circular dichroism. For example, in some embodiments, the peptidomimetic macrocycles of the invention exhibit at least a 1.25, 1.5, 1.75 or 2-fold increase in $\alpha$-helicity as determined by circular dichroism compared to a corresponding non-macrocyclic polypeptide.

The term "$\alpha$-amino acid" or simply "amino acid" refers to a molecule containing both an amino group and a carboxyl group bound to a carbon which is designated the $\alpha$-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" refers to a molecule which is structurally similar to an amino acid and which can be substituted for an amino acid in the formation of a peptide or peptidomimetic macrocycle. Amino acid analogs include compounds which are structurally identical to an amino acid, as defined herein, except for the inclusion of one or more additional methylene groups between the amino and carboxyl group (e.g., $\alpha$-amino $\beta$-carboxy acids), or for the substitution of the amino or carboxy group by a similarly reactive group (e.g., substitution of the primary amine with a secondary or tertiary amine, or substitution or the carboxy group with an ester).

A "non-essential" amino acid residue is a residue that can be altered from the wild-type sequence of a polypeptide (e.g., a BH3 domain or the p53 MDM2 binding domain) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a BH3 polypeptide, for example, is preferably replaced with another amino acid residue from the same side chain family.

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol "⫽" when used as part of a molecular structure refers to a single bond or a trans or cis double bond.

The term "amino acid side chain" refers to a moiety attached to the $\alpha$-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an $\alpha,\alpha$ di-substituted amino acid).

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acids sequences (e.g., fragments of naturally occurring proteins or synthetic polypeptide fragments).

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl, "Arylamido" refers to an aryl group, as defined above, wherein one of the aryl group's hydrogen atoms has been replaced with one or more —C(O)$NH_2$ groups. Representative examples of an arylamido group include 2-C(O)NH2-phenyl, 3-C(O)$NH_2$-phenyl, 4-C(O)$NH_2$-phenyl, 2-C(O)$NH_2$-pyridyl, 3-C(O)$NH_2$-pyridyl, and 4-C(O)$NH_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —$CH_2CH_2$-morpholine, —$CH_2CH_2$-piperidine, —$CH_2CH_2CH_2$-morpholine, and —$CH_2CH_2CH_2$-imidazole.

"Alkylamido" refers to a $C_1$-$C_5$ alkyl group, as defined above, wherein one of the $C_1$-$C_5$ alkyl group's hydrogen atoms has been replaced with a —C(O)$NH_2$ group. Representative examples of an alkylamido group include, but are not limited to, —$CH_2$—C(O)$NH_2$, —$CH_2CH_2$—C(O)$NH_2$, —$CH_2CH_2CH_2$C(O)$NH_2$, —$CH_2CH_2CH_2CH_2$C(O)$NH_2$, —$CH_2CH_2CH_2CH_2CH_2$C(O)$NH_2$, —$CH_2$CH(C(O)$NH_2$)$CH_3$, —$CH_2$CH(C(O)$NH_2$)$CH_2CH_3$, —CH(C(O)$NH_2$)$CH_2CH_3$ and —C($CH_3$)$_2CH_2$C(O)$NH_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —$CH_2$OH, —$CH_2CH_2$OH, —$CH_2CH_2CH_2$OH, —$CH_2CH_2CH_2CH_2$OH, —$CH_2CH_2CH_2$ $CH_2CH_2$OH, —$CH_2$CH(OH)$CH_3$, —$CH_2$CH(OH)$CH_2CH_3$, —CH(OH)$CH_3$ and —C($CH_3$)$_2CH_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —$CH_2$COOH, —$CH_2CH_2$COOH, —$CH_2CH_2CH_2$COOH, —$CH_2CH_2CH_2CH_2$COOH, —$CH_2$CH(COOH)$CH_3$, —$CH_2CH_2CH_2CH_2CH_2$COOH, —$CH_2$CH(COOH)$CH_2CH_3$, —CH(COOH)$CH_2CH_3$ and —C($CH_3$)$_2CH_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., $p<0.1$) increase or decrease of at least 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or."

The details of one or more particular embodiments of the invention are set forth in the accompanying drawings and the description below. Other features, objects, and advantages of the invention will be apparent from the description and drawings, and from the claims.

Peptidomimetic Macrocycles of the Invention

The present invention provides peptidomimetic macrocycles of Formula (I):

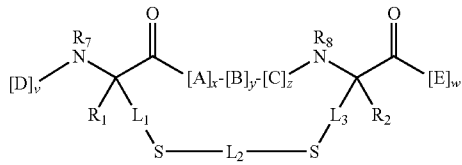

Formula I wherein:
each A, C, D, and E is independently a natural or non-natural amino acid;
B is a natural or non-natural amino acid, amino acid analog,

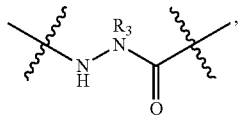

[—NH-$L_4$-CO—], [—NH-$L_4$-$SO_2$—], or [—NH-$L_4$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;
$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, unsubstituted or substituted with $R_5$;
$L_1$, $L_2$, $L_3$ and $L_4$ are independently alkylene, alkenylene, alkynylene, heteroalkylene, cycloalkylene, heterocycloalkylene, cycloarylene, heterocycloarylene or [—$R_4$—K—$R_4$-]n, each being unsubstituted or substituted with $R_5$;
K is O, S, SO, $SO_2$, CO, $CO_2$, or $CONR_3$;
each $R_4$ is alkylene, alkenylene, alkynylene, heteroalkylene, cycloalkylene, heterocycloalkylene, arylene, or heteroarylene;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
$R_7$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with a D residue;
$R_8$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with an E residue;
v is an integer from 1-1000;
w is an integer from 1-1000;
x is an integer from 0-10;
y is an integer from 0-10;
z is an integer from 0-10; and
n is an integer from 1-5.

In some embodiments of the invention, x+y+z is at least 3. In other embodiments of the invention, x+y+z is 3, 4, 5, 6, 7, 8, 9 or 10. Each occurrence of A, B, C, D or E in a macrocycle or macrocycle precursor of the invention is independently selected. For example, a sequence represented by the formula $[A]_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and $R_8$ is —H, allowing intrahelical hydrogen bonding.

In other embodiments, the length of the macrocycle-forming linker [-$L_1$-S-$L_2$-S $L_3$-] as measured from a first Cα to a second Cα is selected to stabilize a desired secondary peptide structure, such as an α-helix formed by residues of the peptidomimetic macrocycle including, but not necessarily limited to, those between the first Cα to a second Cα.

In some embodiments, the peptidomimetic macrocycle comprises at least one α-helix motif. For example, A, B and/or C in the compound of Formula I include one or more α-helices. As a general matter, α-helices include between 3 and 4 amino acid residues per turn. In some embodiments, the α-helix of the peptidomimetic macrocycle includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the peptidomimetic macrocycle. Thus, in some embodiments, the length of the macrocycle-forming linker [-$L_1$-S-$L_2$-S-$L_3$-] from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In other embodiments, D and/or E are further modified in order to facilitate cellular uptake. For example, lipidating or PEGylating a peptide facilitates in some embodiments cellular uptake, increase bioavailability, increase blood circulation, alter pharmacokinetics, decrease immunogenicity and/or decrease the needed frequency of administration.

The synthesis of the peptidomimetic macrocycles of the invention involves a multi-step process that features the (1) synthesis of a precursor peptide or peptidomimetic containing two free —SH moieties; and (2) then contacting the precursor with a bis-alkylating reagent to generate two new covalent bonds.

Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985. In some embodiments, the thiol moieties are the side chains of the amino acid residues L-cysteine, D-cysteine, α-methyl-L cysteine, α-methyl-D-cysteine, L-homocysteine, D-homocysteine, α-methyl-L-homocysteine or α-methyl-D-homocysteine. The bis-alkylating reagent is of the general formula $X-L_2-Y$ wherein $L_2$ is a linker moiety and X and Y are leaving groups that are displaced by —SH moieties to form bonds with $L_2$. In some embodiments, X and Y are halogens such as I, Br, or Cl.

In one embodiment, the peptidomimetic macrocycle exhibits improved biological properties such as increased structural stability, increased affinity for a target, increased resistance to proteolytic degradation and/or increased cell penetrance when compared to the precursor peptide or peptidomimetic. In another embodiment, the peptidomimetic macrocycle comprises one or more α-helices in aqueous solutions and/or exhibits an increased degree of α-helicity when compared to the precursor peptide or peptidomimetic. The method provides a route towards the synthesis of a library of peptidomimetic macrocycles by varying the $X-L_2-Y$ reagent, and in some embodiments the linker element $L_2$ is optimized to improve the biological or pharmacological properties of the resultant peptidomimetic macrocycle.

In some embodiments, the macrocycle-forming linker increases cell permeability of the peptidomimetic macrocycle. Thus, in some embodiments, the macrocycle-forming linker increases the overall hydrophobicity of the peptidomimetic macrocycle relative to the precursor peptide or peptidomimetic.

Any protein or polypeptide with a known primary amino acid sequence which contains a secondary structure believed to impart biological activity is the subject of the present invention. For example, the sequence of the polypeptide can be analyzed and the sulfhydryl containing amino acid analogs of the invention can be substituted at the appropriate positions. The appropriate positions are determined by ascertaining which molecular surface(s) of the secondary structure is (are) required for biological activity and, therefore, across which other surface(s) the macrocycle forming linkers of the invention can form a macrocycle without sterically blocking the surface(s) required for biological activity. Such determinations are made using methods such as X-ray crystallography of complexes between the secondary structure and a natural binding partner to visualize residues (and surfaces) critical for activity; by sequential mutagenesis of residues in the secondary structure to functionally identify residues (and surfaces) critical for activity; or by other methods. By such determinations, the appropriate amino acids are substituted with the amino acids analogs and macrocycle-forming linkers of the invention. For example, for an α-helical secondary structure, one surface of the helix (e.g., a molecular surface extending longitudinally along the axis of the helix and radially 45-135° about the axis of the helix) may be required to make contact with another biomolecule in vivo or in vitro for biological activity. In such a case, a macrocycle-forming linker is designed to link two α-carbons of the helix while extending longitudinally along the surface of the helix in the portion of that surface not directly required for activity.

In some embodiments of the invention, the peptide sequence is derived from the BCL-2 family of proteins. The BCL-2 family is defined by the presence of up to four conserved BCL-2 homology (BH) domains designated BH1, BH2, BH3, and BH4, all of which include α-helical segments (Chittenden et al. (1995), *EMBO* 14:5589; Wang et al. (1996), *Genes Dev.* 10:2859). Anti-apoptotic proteins, such as BCL-2 and $BCL-X_L$, display sequence conservation in all BH domains. Pro-apoptotic proteins are divided into "multidomain" family members (e.g., BAK, BAX), which possess homology in the BH1, BH2, and BH3 domains, and "BH3-domain only" family members (e.g., BID, BAD, BIM, BIK, NOXA, PUMA), that contain sequence homology exclusively in the BH3 amphipathic α-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. Additional "security" measures include regulating transcription of pro-apoptotic proteins and maintaining them as inactive conformers, requiring either proteolytic activation, dephosphorylation, or ligand-induced conformational change to activate pro-death functions. In certain cell types, death signals received at the plasma membrane trigger apoptosis via a mitochondrial pathway. The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-$X_L$ and BAK/BAX play dueling roles of guardian and executioner at the mitochondrial membrane, with their activities further regulated by upstream BH3-only members of the BCL-2 family. For example, BID is a member of the BH3-domain only family of pro-apoptotic proteins, and transmits death signals received at the plasma membrane to effector pro-apoptotic proteins at the mitochondrial membrane. BID has the capability of interacting with both pro- and anti-apoptotic proteins, and upon activation by caspase 8, triggers cytochrome c release and mitochondrial apoptosis. Deletion and mutagenesis studies determined that the amphipathic α-helical BH3 segment of pro-apoptotic family members functions as a death domain and thus represents a critical structural motif for interacting with multidomain apoptotic proteins. Structural studies have demonstrated that the BH3 helix interacts with anti-apoptotic proteins by inserting into a hydrophobic groove formed by the interface of BH1, 2 and 3 domains. Activated BID can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program. BAD is also a BH3-domain only pro-apoptotic family member whose expression triggers the activation of BAX/BAK. In contrast to BID, however, BAD displays preferential binding to anti-apoptotic family members, BCL-2 and BCL-$X_L$. Whereas the BAD BH3 domain exhibits high affinity binding to BCL-2, BAD BH3 peptide is unable to activate cytochrome c release from mitochondria in vitro, suggesting that BAD is not a direct activator of BAX/BAK. Mitochondria that over-express BCL-2 are resistant to BID-induced cytochrome c release, but co-treatment with BAD can restore BID sensitivity. Induction of mitochondrial apoptosis by BAD appears to result from either: (1) displacement of BAX/BAK activators, such as BID and BID-like proteins, from the BCL-2/BCL-XL binding pocket, or (2) selective occupation of the BCL-2/BCL-XL binding pocket by BAD to prevent sequestration of BID-like proteins by anti-apoptotic proteins. Thus, two classes of BH3-domain only proteins have emerged, BID-like proteins that directly activate mitochondrial apoptosis, and BAD-like proteins, that have the capacity to sensitize mitochondria to BID-like pro-apoptotics by occupying the binding pockets of multidomain anti-apoptotic proteins. Various α-helical domains of BCL-2 family member proteins amendable to the methodology disclosed herein have been disclosed (Walensky et al. (2004), *Science* 305:1466; and Walensky et al., U.S. Patent Publication No. 2005/0250680, the entire disclosures of which are incorporated herein by reference).

In other embodiments, the peptide sequence is derived from the tumor suppressor p53 protein which binds to the oncogene protein MDM2. The MDM2 binding site is localized within a region of the p53 tumor suppressor that forms an a helix. In U.S. Pat. No. 7,083,983, the entire contents of which are incorporated herein by reference, Lane et al. disclose that the region of p53 responsible for binding to MDM2 is represented approximately by amino acids 13-31 (PLSQETFSDLWKLLPENNV)(SEQ ID NO: 1) of mature human P53 protein. Other modified sequences disclosed by Lane are also contemplated in the instant invention. Furthermore, the interaction of p53 and MDM2 has been discussed by Shair et al. (1997), *Chem. & Biol.* 4:791, the entire contents of which are incorporated herein by reference, and mutations in the p53 gene have been identified in virtually half of all reported cancer cases. As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic α-helix of 2.5 turns that inserts into the MDM2 crevice. Thus, in some embodiments, novel α-helix structures generated by the method of the present invention are engineered to generate structures that bind tightly to the helix acceptor and disrupt native protein-protein interactions. These structures are then screened using high throughput techniques to identify optimal small molecule peptides. The novel structures that disrupt the MDM2 interaction are useful for many applications, including, but not limited to, control of soft tissue sarcomas (which overexpresses MDM2 in the presence of wild type p53). These cancers are then, in some embodiments, held in check with small molecules that intercept MDM2, thereby preventing suppression of p53. Additionally, in some embodiments, small molecules disrupters of MDM2-p53 interactions are used as adjuvant therapy to help control and modulate the extent of the p53 dependent apoptosis response in conventional chemotherapy.

A non-limiting exemplary list of suitable peptides for use in the present invention is given below:

TABLE 1[1]

| Name BH3 peptides | Sequence (bold = critical residues) (SEQ ID NOS 2-24 disclosed respectively in order of appearance) | Cross-linked Sequence (X = x-link residue) (SEQ ID NOS 25-47 disclosed respectively in order of appearance) |
|---|---|---|
| BID-BH3 | QEDIIRNIARHLAQVGDSMDRSIPP | QEDIIRNIARHLAXVGDXMDRSIPP |
| BIM-BH3 | DNRPEIWIAQELRRIGDEFNAYYAR | DNRPEIWIAQELRXIGDXFNAYYAR |

TABLE 1[1] -continued

| Name BH3 peptides | Sequence (bold = critical residues) (SEQ ID NOS 2-24 disclosed respectively in order of appearance) | Cross-linked Sequence (X = x-link residue) (SEQ ID NOS 25-47 disclosed respectively in order of appearance) |
| --- | --- | --- |
| BAD-BH3 | NLWAAQRYGRELRRMSDEFVDSFKK | NLWAAQRYGREL RXMSDXFVDSFKK |
| PUMA-BH3 | EEQWAREIGAQLRRMADDLNAQYER | EEQWAREIGAQLRXMADXLNAQYER |
| Hrk-BH3 | RSSAAQLTAARLKALGDELHQRTM | RSSAAQLTAARLKXLGDXLHQRTM |
| NOXAA-BH3 | AELPPEFAAQLRKIGDKVYCTW | AELPPEFAAQLRXIGDXVYCTW |
| NOXAB-BH3 | VPADLKDECAQLRRIGDKVNLRQKL | VPADLKDECAQLRXIGDXVNLRQKL |
| BMF-BH3 | QHRAEVQIARKLQCIADQFHRLHT | QHRAEVQIARKLQXIADXFHRLHT |
| BLK-BH3 | SSAAQLTAARLKALGDELHQRT | SSAAQLTAARLKXLGDXLHQRT |
| BIK-BH3 | CMEGSDALALRLACIGDEMDVSLRA | CMEGSDALALRLAXIGDXMDVSLRA |
| Bnip3 | DIERRKEVESILKKNSDWIWDWSS | DIERRKEVESILKXNSDXIWDWSS |
| BOK-BH3 | GRLAEVCAVLLRLGDELEMIRP | GRLAEVCAVLLXLGDXLEMIRP |
| BAX-BH3 | PQDASTKKSECLKRIGDELDSNMEL | PQDASTKKSECLKXIGDXLDSNMEL |
| BAK-BH3 | PSSTMGQVGRQLAIIGDDINRR | PSSTMGQVGRQLAXIGDXINRR |
| BCL2L1-BH3 | KQALREAGDEFELR | KQALRXAGDXFELR |
| BCL2-BH3 | LSPPVVHLALALRQAGDDFSRR | LSPPVVHLALALRXAGDXFSRR |
| BCL-XL-BH3 | EVIPMAAVKQALREAGDEFELRY | EVIPMAAVKQALRXAGDXFELRY |
| BCL-W-BH3 | PADPLHQAMRAAGDEFETRF | PADPLHQAMRXAGDXFETRF |
| MCL1-BH3 | ATSRKLETLRRVGDGVQRNHETA | ATSRKLETLRXVGDXVQRNHETA |
| MTD-BH3 | LAEVCTVLLRLGDELEQIR | LAEVCTVLLXLGDXLEQIR |
| MAP-1-BH3 | MTVGELSRALGHENGSLDP | MTVGELSRALGXENGXLDP |
| NIX-BH3 | VVEGEKEVEALKKSADWVSDWS | VVEGEKEVEALKXSADXVSDWS |
| 4ICD(ERBB4)-BH3 | SMARDPQRYLVIQGDDRMKL | SMARDPQRYLVXQGDXRMKL |

[1]Peptide sequences listed in Table 1 are human sequences which target the BH3 binding site and are implicated in cancers, autoimmune disorders, metabolic diseases and other human disease conditions.

TABLE 2[1]

| Name BH3 peptides | Sequence (bold = critical vsidues) (SEQ ID NOS 2-24 disclosed respectively in order of appearance) | Cross-linked Sequence (X = x-link residue) (SEQ ID NOS 48-70 disclosed respectively in order of appearance) |
| --- | --- | --- |
| BID-BH3 | QEDIIRNIARHLAQVGDSMDRSIPP | QEDIIRNIXRHLXQVGDSMDRSIPP |
| BIM-BH3 | DNRPEIWIAQELRRIGDEFNAYYAR | DNRPEIWIXQELXRIGDEFNAYYAR |
| BAD-BH3 | NLWAAQRYGRELRRMSDEFVDSFKK | NLWAAQRYXRELXRMSDEFVDSFKK |
| PUMA-BH3 | EEQWAREIGAQLRRMADDLNAQYER | EEQWAREIXAQLXRMADDLNAQYER |
| Hrk-BH3 | RSSAAQLTAARLKALGDELHQRTM | RSSAAQLTXARLXALGDELHQRTM |
| NOXAA-BH3 | AELPPEFAAQLRKIGDKVYCTW | AELPPEFXAQLXKIGDKVYCTW |
| NOXAB-BH3 | VPADLKDECAQLRRIGDKVNLRQKL | VPADLKDEXAQLXRIGDKVNLRQKL |
| BMF-BH3 | QHRAEVQIARKLQCIADQFHRLHT | QHRAEVQIXRKLXCIADQFHRLHT |
| BLK-BH3 | SSAAQLTAARLKALGDELHQRT | SSAAQLTXARLXALGDELHQRT |
| BIK-BH3 | CMEGSDALALRLACIGDEMDVSLRA | CMEGSDALXLRLXCIGDEMDVSLRA |

TABLE 2[1] -continued

| Name BH3 peptides | Sequence (bold = critical vsidues) (SEQ ID NOS 2-24 disclosed respectively in order of appearance) | Cross-linked Sequence (X = x-link residue) (SEQ ID NOS 48-70 disclosed respectively in order of appearance) |
|---|---|---|
| Bnip3 | DIERRKEVESILKKNSDWIWDWSS | DIERRKEVXSILXKNSDWIWDWSS |
| BOK-BH3 | GRLAEVCAVLLRLGDELEMIRP | GRLAEVXAVLXRLGDELEMIRP |
| BAX-BH3 | PQDASTKKSECLKRIGDELDSNMEL | PQDASTKKXECLXRIGDELDSNMEL |
| BAK-BH3 | PSSTMGQVGRQLAIIGDDINRR | PSSTMGQVXRQLXIIGDDINRR |
| BCL2L1-BH3 | KQALREAGDEFELR | XQALXEAGDEFELR |
| BCL2-BH3 | LSPPVVHLALALRQAGDDFSRR | LSPPVVHLXLALXQAGDDFSRR |
| BCL-XL-BH3 | EVIPMAAVKQALREAGDEFELRY | EVIPMAAVXQALXEAGDEFELRY |
| BCL-W-BH3 | PADPLHQAMRAAGDEFETRF | PADPLXQAMXAAGDEFETRF |
| MCL1-BH3 | ATSRKLETLRRVGDGVQRNHETA | ATSRKXETLXRVGDGVQRNHETA |
| MTD-BH3 | LAEVCTVLLRLGDELEQIR | LAEVXTVLXRLGDELEQIR |
| MAP-1-BH3 | MTVGELSRALGHENGSLDP | MTVGELXRALXHENGSLDP |
| NIX-BH3 | VVEGEKEVEALKKSADWVSDWS | VVEGEKEXEALXKSADWVSDWS |
| 4ICD(ERBB4)-BH3 | SMARDPQRYLVIQGDDRMKL | SMARDPXRYLXIQGDDRMKL |

[1]Peptide sequences listed in Table 2 are human sequences which target the BH3 binding site and are implicated in cancers, autoimmune disorders, metabolic diseases and other human disease conditions.

TABLE 3[1]

| Name P53 peptides | Sequence (bold = critical residues) | Cross-linked Sequence (X = x-link residue) |
|---|---|---|
| hp53 peptide_veryshort | LSQETFSDLWKLLPEN (SEQ ID NO: 71) | XSQEXFSDLWKLLPEN (SEQ ID NO: 76) |
| hp53 peptide_short | PPLSQETFSDLWKLLPENN (SEQ ID NO: 72) | PPXSQEXFSDLWKLLPENN (SEQ ID NO: 77) |
| hp53-P27S peptide-short | PPLSQETFSDLWKLLSENN (SEQ ID NO: 73) | PPXSQEXFSDLWKLLSENN (SEQ ID NO: 78) |
| hp53 peptide_Long | DPSVEPPLSQETFSDLWKLLPENNVLSPLP (SEQ ID NO: 74) | DPSVEPPXSQEXFSDLWKLLPENNVLSPLP (SEQ ID NO: 79) |
| hp53-P27S peptide_Long | DPSVEPPLSQETFSDLWKLLSENNVLSPLP (SEQ ID NO: 75) | DPSVEPPXSQEXFSDLWKLLSENNVLSPLP (SEQ ID NO: 80) |
| hp53 peptide_veryshort | LSQETFSDLWKLLPEN (SEQ ID NO: 71) | LSQETFSDLWXLLPXN (SEQ ID NO: 81) |
| hp53 peptide_short | PPLSQETFSDLWKLLPENN (SEQ ID NO: 72) | PPLSQETFSDLWXLLPXNN (SEQ ID NO: 82) |
| hp53-P27S peptide-short | PPLSQETFSDLWKLLSENN (SEQ ID NO: 73) | PPLSQETFSDLWXLLSXNN (SEQ ID NO: 83) |
| hp53 peptide_Long | DPSVEPPLSQETFSDLWKLLPENNVLSPLP (SEQ ID NO: 74) | DPSVEPPLSQETFSDLWXLLPXNNVLSPLP (SEQ ID NO: 84) |
| hp53-P27S peptide_Long | DPSVEPPLSQETFSDLWKLLSENNVLSPLP (SEQ ID NO: 75) | DPSVEPPLSQETFSDLWXLLSXNNVLSPLP (SEQ ID NO: 85) |

[1]Peptide sequences listed in Table 3 are human sequences which target the p53 binding site of mdm2/x and are implicated in cancers.

TABLE 4[1]

| Name GPCR peptide ligands (bold = critical residues) | Sequence | Cross-linked Sequence (X = x-link residue) |
|---|---|---|
| Angiotensin II | DRVYIHPF (SEQ ID NO: 86) | DRXYXHPF (SEQ ID NO: 92) |
| Bombesin | EQRLGNQWAVGHLM (SEQ ID NO: 87) | EQRLGNXWAVGHLX (SEQ ID NO: 93) |
| Bradykinin | RPPGFSPFR (SEQ ID NO: 88) | RPPXFSPFRX (SEQ ID NO: 94) |
| C5a | ISHKDMQLGR (SEQ ID NO: 89) | ISHKDMXLGRX (SEQ ID NO: 95) |
| C3a | ARASHLGLAR (SEQ ID NO: 90) | ARASHLXLARX (SEQ ID NO: 96) |
| α-melanocyte stimulating hormone | SYSMEHFRWGKPV (SEQ ID NO: 91) | SYSMXHFRWXKPV (SEQ ID NO: 97) |

[1] Peptide sequences listed in Table 4 are sequences which target human G protein-coupled receptors and are implicated in numerous human disease conditions (Tyndall, J.D.A. et al. Chem. Rev. 2005, 105, 793-826).

Methods of Synthesizing the Peptidomimetic Macrocycles of the Invention

Methods of synthesizing the peptidomimetic macrocycles of the invention are disclosed herein. Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis*, 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The peptidomimetic macrocycles of the invention are made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the precursor peptides and peptidomimetics described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer precursor peptides are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a precursor peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The precursor peptides and peptidomimetics are made, for example, in a high-throughput, combinatorial fashion using, for example, a high-throughput polychannel combinatorial synthesizer (e.g., Model Apex 396 multichannel peptide synthesizer from AAPPTEC, Inc., Louisville, Ky.).

The discussion below is offered to illustrate certain of the diverse methods available for use in assembling the compounds of the invention. However, the discussion is not intended to limit the scope of reactions or reaction sequences that are useful in preparing the compounds of the present invention.

The following synthetic schemes are provided solely to illustrate the present invention and are not intended to limit the scope of the invention, as described herein. To simplify the drawings, the illustrative schemes depict amino acid analogs derived from L- or D-cysteine, in which $L_1$ and $L_3$ are both —$(CH_2)$—. However, as noted throughout the detailed description above, many other amino acid analogs can be employed in which $L_1$ and $L_3$ can be independently selected from the various structures disclosed herein. The symbols "$[AA]_m$", "$[AA]_n$", "$[AA]_o$" represent a sequence of amide bond-linked moieties such as natural or unnatural amino acids. As described previously, each occurrence of "AA" is independent of any other occurrence of "AA", and a formula such as "$[AA]_m$" encompasses, for example, sequences of non-identical amino acids as well as sequences of identical amino acids.

Synthetic Scheme 1:

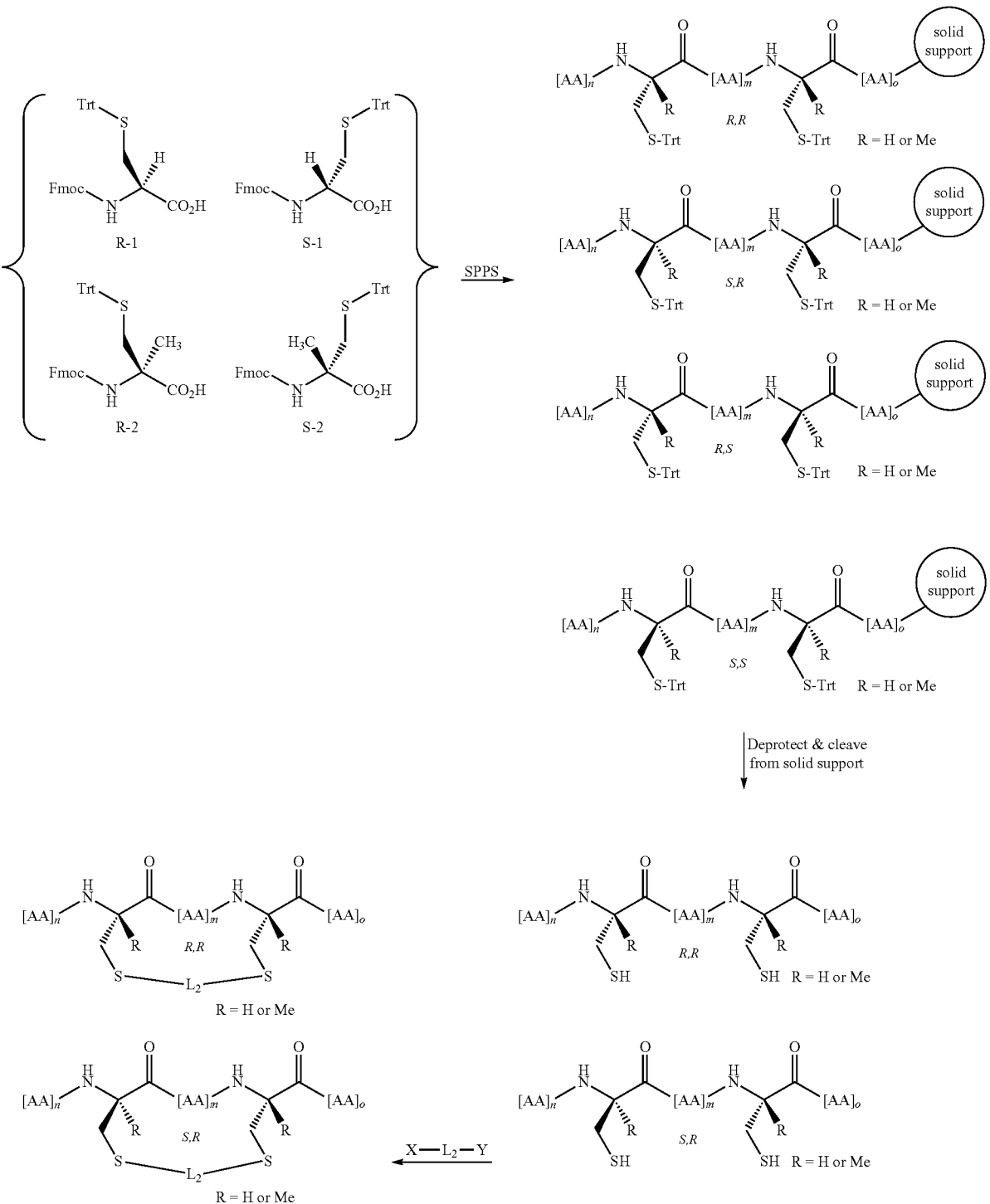

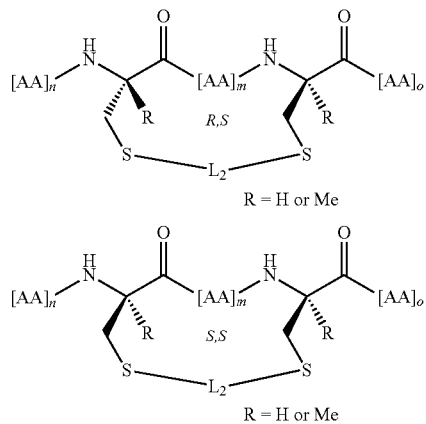

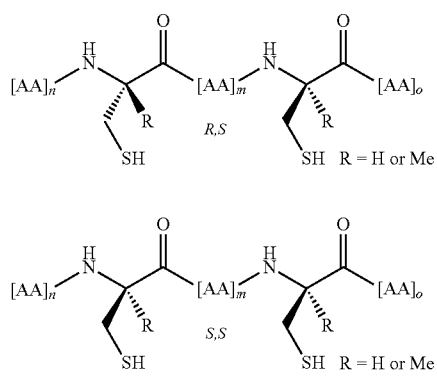

In this first general method, the peptidomimetic precursor contains two —SH moieties and is synthesized by solid-phase peptide synthesis (SPPS) using commercially available N-α-Fmoc amino acids such as N-α-Fmoc-S-trityl-L-cysteine or N-α-Fmoc-S-trityl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-trityl monomers by known methods ("*Bioorganic Chemistry: Peptides and Proteins*", Oxford University Press, New York: 1998, the entire contents of which are incorporated herein by reference). The precursor peptidomimetic is then deprotected and cleaved from the solid-phase resin by standard conditions (e.g., strong acid such as 95% TFA). The precursor peptidomimetic is reacted as a crude mixture or is purified prior to reaction with X-L$_2$-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid NH$_3$ (Mosberg et al. (1985), J. Am. Chem. Soc. 107:2986-2987; Szewczuk et al. (1992), Int. J. Peptide Protein Res. 40:233-242), NH$_3$/MeOH, or NH$_3$/DMF (Or et al. (1991), J. Org. Chem. 56:3146-3149). In other embodiments, the alkylation is performed in an aqueous solution such as 6M guanidinium HCL, pH 8 (Brunel et al. (2005), Chem. Commun. (20):2552-2554). In other embodiments, the solvent used for the alkylation reaction is DMF or dichloroethane.

Synthetic Scheme 2:

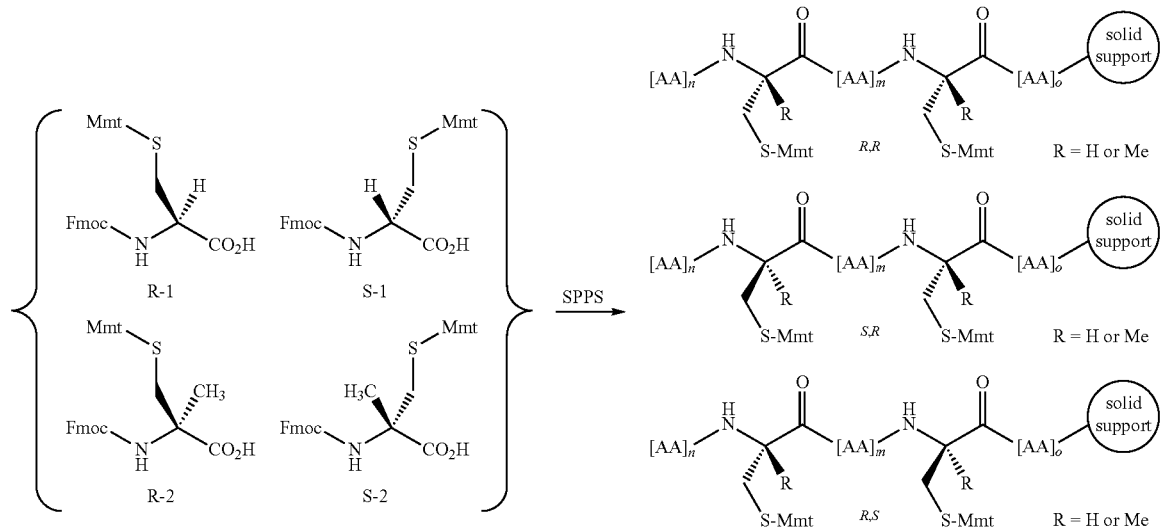

-continued

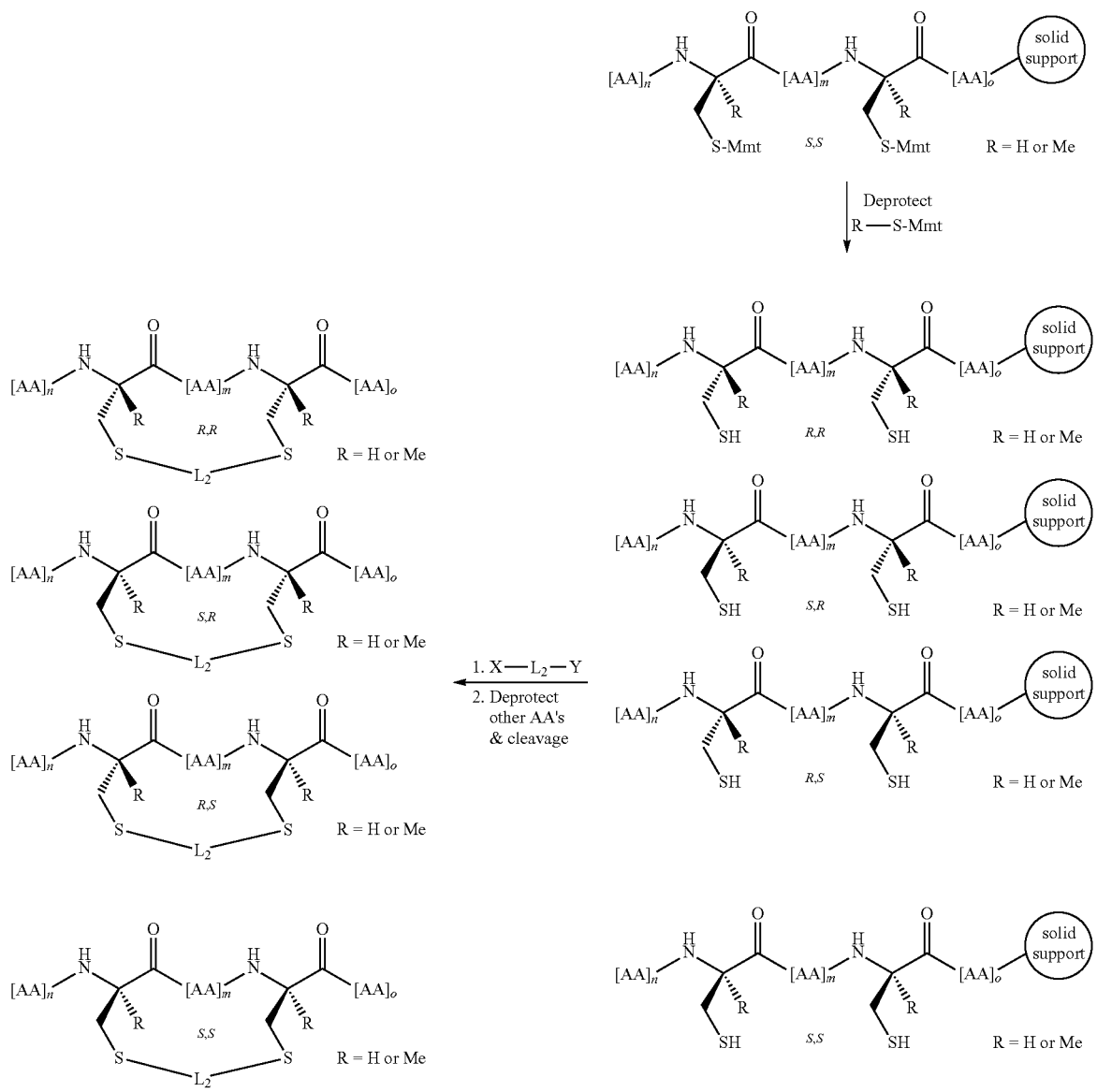

In this second general method, the precursor peptidomimetic contains two or more —SH moieties, of which two are specially protected to allow their selective deprotection and subsequent alkylation for macrocycle formation. The precursor peptidomimetic is synthesized by solid-phase peptide synthesis (SPPS) using commercially available N-α-Fmoc amino acids such as N-α-Fmoc-S-p-methoxytrityl-L-cysteine or N-α-Fmoc-S-p-methoxytrityl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl monomers by known methods (*Bioorganic Chemist: Peptides and Proteins*, Oxford University Press, New York: 1998, the entire contents of which are incorporated herein by reference). The Mmt protecting groups of the peptidomimetic precursor are then selectively cleaved by standard conditions (e.g., mild acid such as 1% TFA in DCM). The precursor peptidomimetic is then reacted on the resin with X-L$_2$-Y in an organic solution. For example, the reaction takes place in the presence of a hindered base such as diisopropylethylamine. In some embodiments, the alkylation reaction is performed in organic solutions such as liquid NH$_3$ (Mosberg et al. (1985), *J. Am. Chem. Soc.* 107:2986-2987; Szewczuk et al. (1992), *Int. J. Peptide Protein Res.* 40:233-242), NH$_3$/MeOH or NH$_3$/DMF (Or et al. (1991), *J. Org. Chem.* 56:3146-3149). In other embodiments, the alkylation reaction is performed in DMF or dichloroethane. The peptidomimetic macrocycle is then deprotected and cleaved from the solid-phase resin by standard conditions (e.g., strong acid such as 95% TFA).

Synthetic Scheme 3:

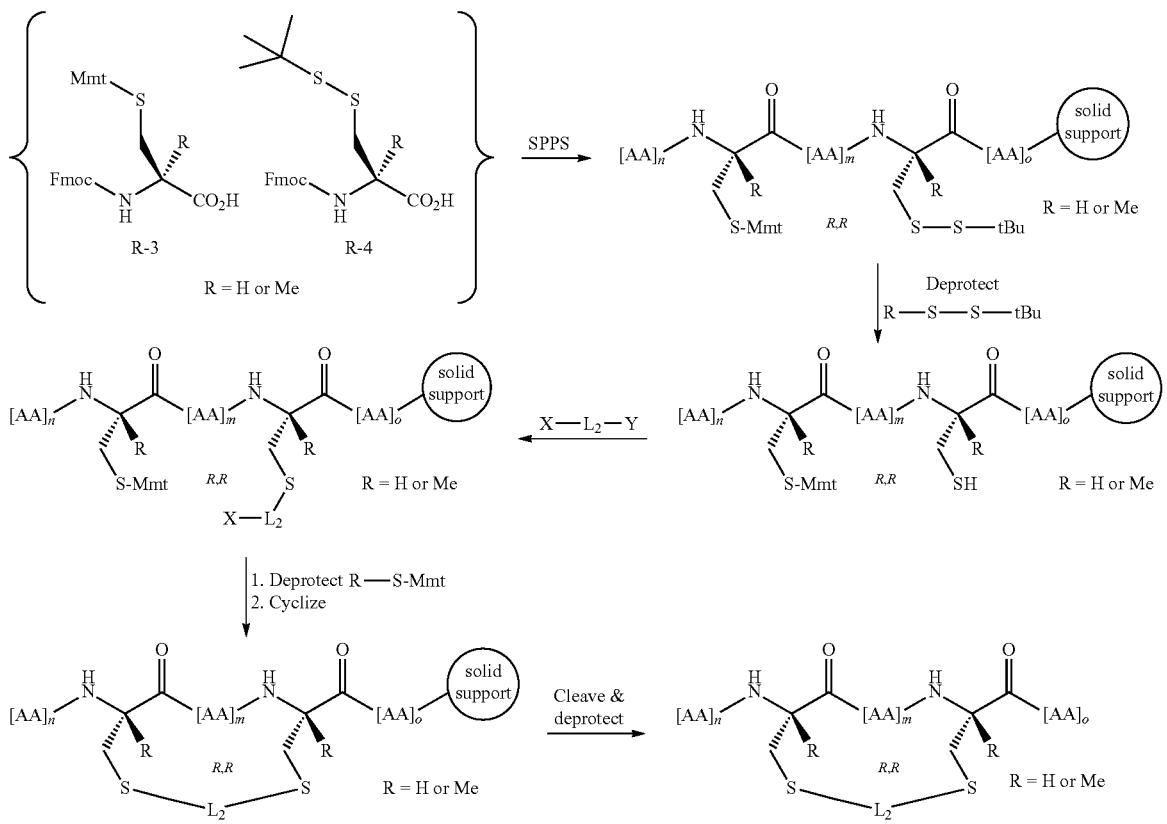

In this third general method, the peptidomimetic precursor contains two or more —SH moieties, of which two are specially protected to allow their selective deprotection and subsequent alkylation for macrocycle formation. The peptidomimetic precursor is synthesized by solid-phase peptide synthesis (SPPS) using commercially available N-α-Fmoc amino acids such as N-α-Fmoc-S-p-methoxytrityl-L-cysteine, N-α-Fmoc-S-p-methoxytrityl-D-cysteine, N-α-Fmoc-S—S-t-butyl-L-cysteine, and N-α-Fmoc-S—S-t-butyl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl or N-α-Fmoc-S—S-t-butyl monomers by known methods (*Bioorganic Chemistry: Peptides and Proteins*, Oxford University Press, New York: 1998, the entire contents of which are incorporated herein by reference). The S—S-tButyl protecting group of the peptidomimetic precursor is selectively cleaved by known conditions (e.g., 20% 2-mercaptoethanol in DMF, reference: Galande et al. (2005), *J. Comb. Chem.* 7:174-177). The precursor peptidomimetic is then reacted on the resin with a molar excess of X-L$_2$-Y in an organic solution. For example, the reaction takes place in the presence of a hindered base such as diisopropylethylamine. The Mmt protecting group of the peptidomimetic precursor is then selectively cleaved by standard conditions (e.g., mild acid such as 1% TFA in DCM). The peptidomimetic precursor is then cyclized on the resin by treatment with a hindered base in organic solutions. In some embodiments, the alkylation reaction is performed in organic solutions such as NH$_3$/MeOH or NH$_3$/DMF (Or et al. (1991),

*J. Org. Chem.* 56:3146-3149). The peptidomimetic macrocycle is then deprotected and cleaved from the solid-phase resin by standard conditions (e.g., strong acid such as 95% TFA).

Synthetic Scheme 4:

1. Biological synthesis of peptide
2. Purification of peptide

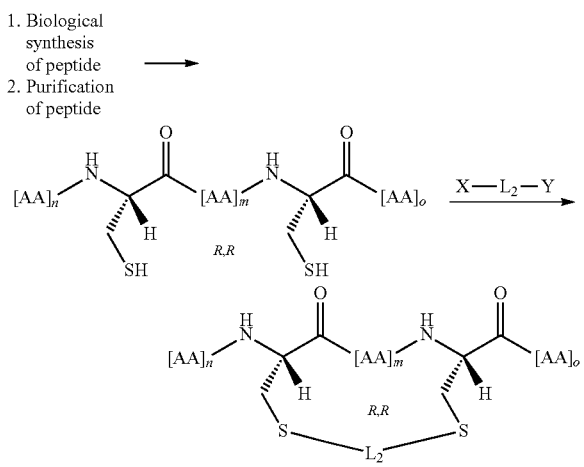

In this fourth general method, the peptidomimetic precursor contains two L-cysteine moieties. The peptidomimetic precursor is synthesized by known biological expression systems in living cells or by known in vitro, cell-free, expression methods. The precursor peptidomimetic is reacted as a crude mixture or is purified prior to reaction with X-L2-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid $NH_3$ (Mosberg et al. (1985), J. Am. Chem. Soc. 107:2986-2987; Szewczuk et al. (1992), Int. J. Peptide Protein Res. 40:233-242), $NH_3$/MeOH, or $NH_3$/DMF (Or et al. (1991), J. Org. Chem. 56:3146-3149). In other embodiments, the alkylation is performed in an aqueous solution such as 6 M guanidinium HCL, pH 8 (Brunel et al. (2005), Chem. Commun. (20):2552-2554). In other embodiments, the alkylation is performed in DMF or dichloroethane. In another embodiment, the alkylation is performed in non-denaturing aqueous solutions, and in yet another embodiment the alkylation is performed under conditions that favor α-helical structure formation. In yet another embodiment, the alkylation is performed under conditions that favor the binding of the precursor peptidomimetic to another protein, so as to induce the formation of the bound α-helical conformation during the alkylation.

Various embodiments for X and Y are envisioned which are suitable for reacting with thiol groups. In general, each X or Y is independently be selected from the general category shown in Table 5. For example, X and Y are halides such as —Cl, —Br or —I.

TABLE 5

Examples of Reactive Groups Capable of Reacting with Thiol Groups and Resulting Linkages

| X or Y | Resulting Covalent Linkage |
|---|---|
| acrylamide | Thioether |
| halide (e.g. alkyl or aryl halide) | Thioether |
| sulfonate | Thioether |
| aziridine | Thioether |
| epoxide | Thioether |
| haloacetamide | Thioether |
| maleimide | Thioether |
| sulfonate ester | Thioether |

Table 6 shows exemplary macrocycles of the invention. For the examples shown in this table, a corresponding non-macrocyclic polypeptide is the BID BH3 polypeptide sequence fragment DIIRNIARHLAQVGDSMDRSI (SEQ ID NO: 98). "$N_L$" represents norleucine and replaces a methionine residue. It is envisioned that similar linkers are used to synthesize peptidomimetic macrocycles based on the polypeptide sequences disclosed in Table 1 through Table 4.

TABLE 6

Examples of Peptidomimetic Macrocycles of the Invention

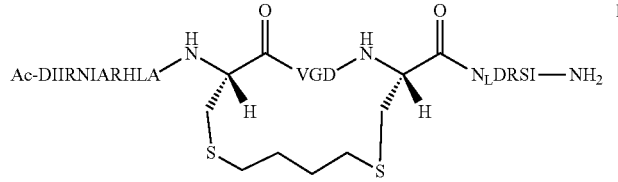

MW = 2449

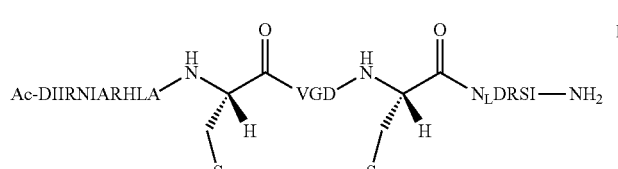

MW = 2435

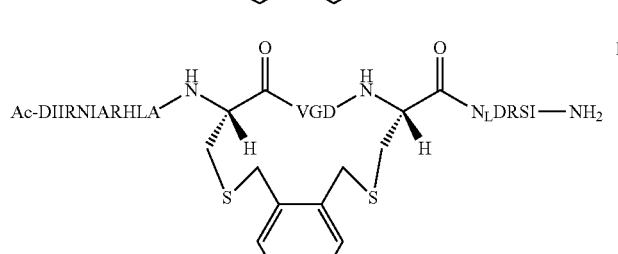

MW = 2497

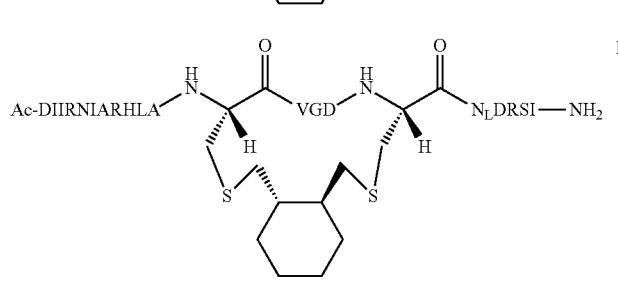

MW = 2503

TABLE 6-continued
Examples of Peptidomimetic Macrocycles of the Invention
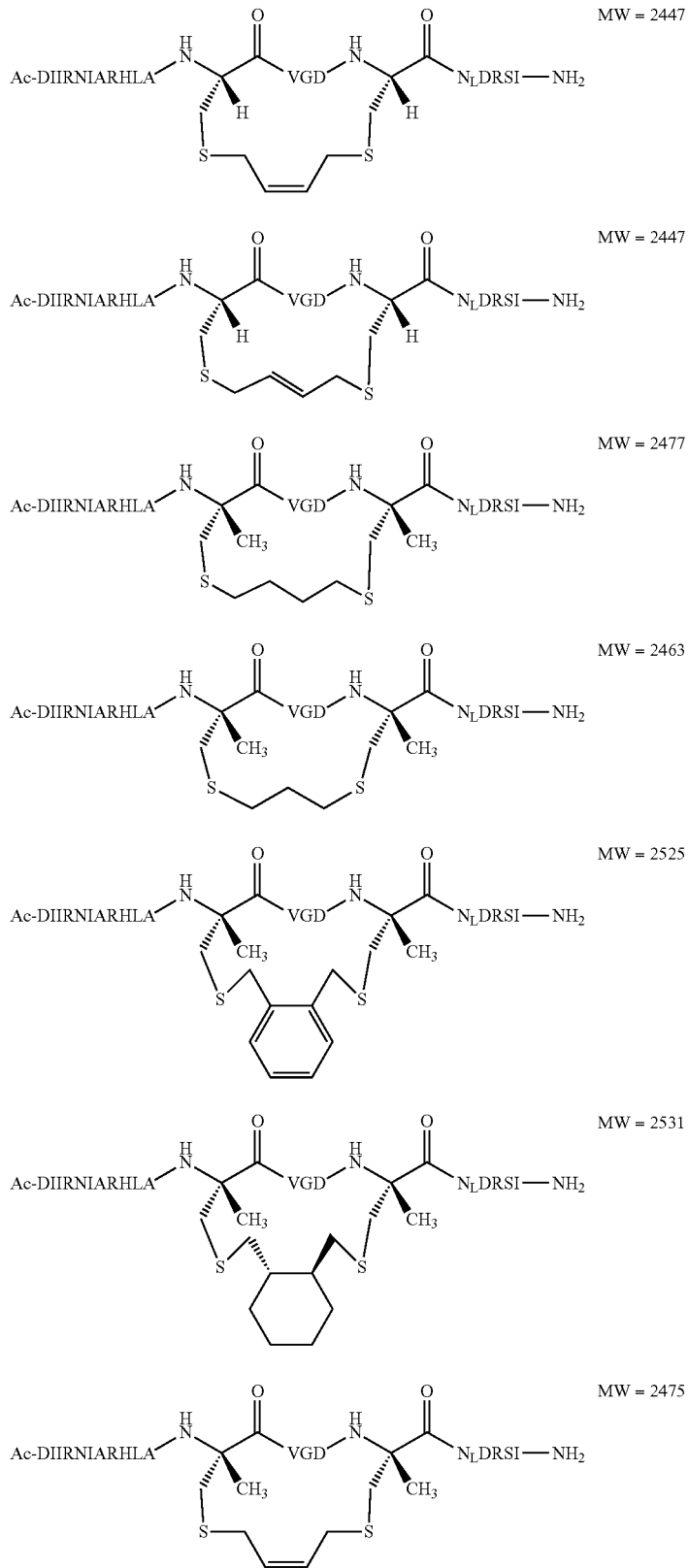

TABLE 6-continued

Examples of Peptidomimetic Macrocycles of the Invention

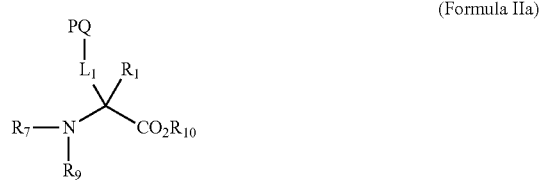

MW = 2475

For the examples shown in this table, a corresponding non-macrocyclic polypeptide is the BID BH3 polypeptide sequence fragment DIIRNIARHLAQVGDSMDRSI (SEQ ID NO: 98).
"$N_L$" represents norleucine. (DIIRNIARHLACVGDCN$_L$DRSI is disclosed as SEQ ID NO: 99)

Amino Acid Analogs

The present invention contemplates the use of both naturally-occurring and non-naturally-occurring amino acids and amino acid analogs in the synthesis of the peptidomimetic macrocycles described above. Any amino acid or amino acid analog amenable to the synthetic methods employed for the synthesis of stable bis-sulfhydryl containing peptidomimetic macrocycles can be used in the present invention. For example, cysteine is contemplated as a useful amino acid in the present invention. However, sulfur containing amino acids other than cysteine that contain a different amino acid side chain are also useful in the invention. For example, cysteine contains one methylene unit between the α-carbon of the amino acid and the terminal —SH of the amino acid side chain. The invention also contemplates the use of amino acids with multiple methylene units between the α-carbon and the terminal —SH. Non-limiting examples include L-homocysteine, D-homocysteine, α-methyl-L-homocysteine and α-methyl-D-homocysteine. In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-cysteine and α-methyl-D-cysteine. In some embodiments the amino acid analogs are N-alkylated, e.g., N-methyl-L-cysteine and N-methyl-D-cysteine.

Other amino acid analogs useful in the present invention for forming peptidomimetic macrocycles are compounds of Formula IIa:

(Formula IIa)

$$\begin{array}{c} PQ \\ | \\ L_1 \quad R_1 \\ | \\ R_7-N \quad CO_2R_{10} \\ | \\ R_9 \end{array}$$

wherein:

$R_1$ is alkyl, alkenyl, alkynyl, arylalkyl, cycloalkyl, cycloalkylalkyl, heteroalkyl, or heterocycloalkyl;

$L_1$ is independently alkylene, alkenylene, alkynylene, heteroalkylene, cycloalkylene, heterocycloalkylene, cycloarylene, heterocycloarylene or [—$R_4$—K—$R_4$-]n, unsubstituted or substituted with $R_5$;

K is O, S, SO, $SO_2$, CO, $CO_2$, or $CONR_3$;

$R_4$ is alkylene, alkenylene, alkynylene, heteroalkylene, cycloalkylene, heterocycloalkylene, arylene, or heteroarylene;

$R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

$R_6$ is independently —H, alkyl, alkenyl, alkynyl, arylalkyl, cycloalkylalkyl, heteroalkylalkyl, heterocyclyalkyl, a fluorescent moiety, a radioisotope or a therapeutic agent;

$R_7$ is —H, alkyl, alkenyl, alkynyl, arylalkyl, cycloalkylalkyl, heteroalkylalkyl, or heterocyclyalkyl;

$R_9$ and $R_{10}$ are independently —H or a protecting group suitable for peptide synthesis; n is an integer from 1 to 5;

Q is S; and

P is —H, -trityl, p-methoxytrityl, —S t-butyl, or any other protecting group suitable for peptide synthesis; or Q and P when taken together form a moiety capable of undergoing chemical transformation into an —SH group.

In some embodiments either the —NH or the —SH moieties of the amino acid are protected. In other embodiments both moieties are protected, for example protecting groups for either the —NH and the —SH moieties in amino acids. Non-limiting examples of such —NH protecting groups are -Fmoc and -Boc. Non-limiting examples of —SH protecting groups are -trityl, p-methoxytrityl, and —S t-butyl. In other embodiments, the amino acid is not protected prior to synthesis of the peptidomimetic macrocycle.

TABLE 7

Exemplary amino acids of the invention.

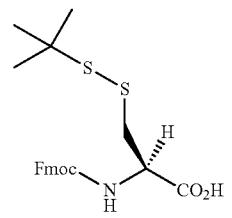

N-α-Fmoc-S-S-t-Bu-L-cysteine

R-α-methyl

TABLE 7-continued

Exemplary amino acids of the invention.

N-α-Fmoc-S-S-t-Bu-cysteine

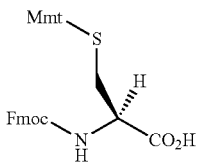

N-α-Fmoc-S-p-methoxytrityl-L-cysteine

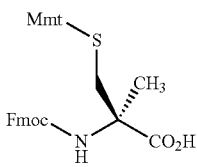

R-α-methyl
N-α-Fmoc-S-p-methoxytrityl-cysteine

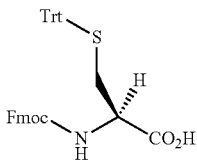

N-α-Fmoc-S-trityl-L-cysteine

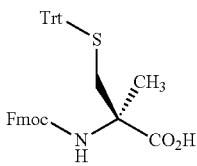

R-α-methyl
N-α-Fmoc-S-trityl-cysteine

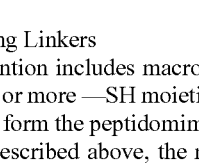

Macrocycle-Forming Linkers

The present invention includes macrocycle-forming linkers used to link two or more —SH moieties in the peptidomimetic precursors to form the peptidomimetic macrocycles of the invention. As described above, the macrocycle-forming linkers impart conformational rigidity, increased metabolic stability and/or increased cell penetrability. Furthermore, in some embodiments, the macrocycle-forming linkages stabilize the α-helical secondary structure of the peptidomimetic macrocycles. The macrocycle-forming linkers are of the formula $X-L_2-Y$, wherein both X and Y are the same or different moieties, as defined above. Both X and Y have the chemical characteristics that allow one macrocycle-forming linker -$L_2$- to bis alkylate the bis-sulfhydryl containing peptidomimetic precursor. As defined above, the linker -$L_2$- includes alkylene, alkenylene, alkynylene, heteroalkylene, cycloalkylene, heterocycloalkylene, cycloarylene, or heterocycloarylene, or —$R_4$—K—$R_4$—, all of which can be optionally substituted with an $R_5$ group, as defined above. Furthermore, one to three carbon atoms within the macrocycle-forming linkers -$L_2$-, other than the carbons attached to the —SH of the sulfhydryl containing amino acid, are optionally substituted with a heteroatom such as N, S or O.

The $L_2$ component of the macrocycle-forming linker $X-L_2-Y$ may be varied in length depending on, among other things, the distance between the positions of the two amino acid analogs used to form the peptidomimetic macrocycle. Furthermore, as the lengths of $L_1$ and/or $L_3$ components of the macrocycle-forming linker are varied, the length of $L_2$ can also be varied in order to create a linker of appropriate overall length for forming a stable peptidomimetic macrocycle. For example, if the amino acid analogs used are varied by adding an additional methylene unit to each of $L_1$ and $L_3$, the length of $L_2$ are decreased in length by the equivalent of approximately two methylene units to compensate for the increased lengths of $L_1$ and $L_3$.

In some embodiments, $L_2$ is an alkylene group of the formula —$(CH_2)_n$—, where n is an integer between about 1 and about 15. For example, n is 1, 2, 3, 4, 5, 6, 7, 8, 9 or 10. In other embodiments, $L_2$ is an alkenylene group. In still other embodiments, $L_2$ is an aryl group.

Table X shows additional embodiments of X-$L_2$-Y groups.

TABLE 8

Exemplary X—$L_2$—Y groups of the invention.

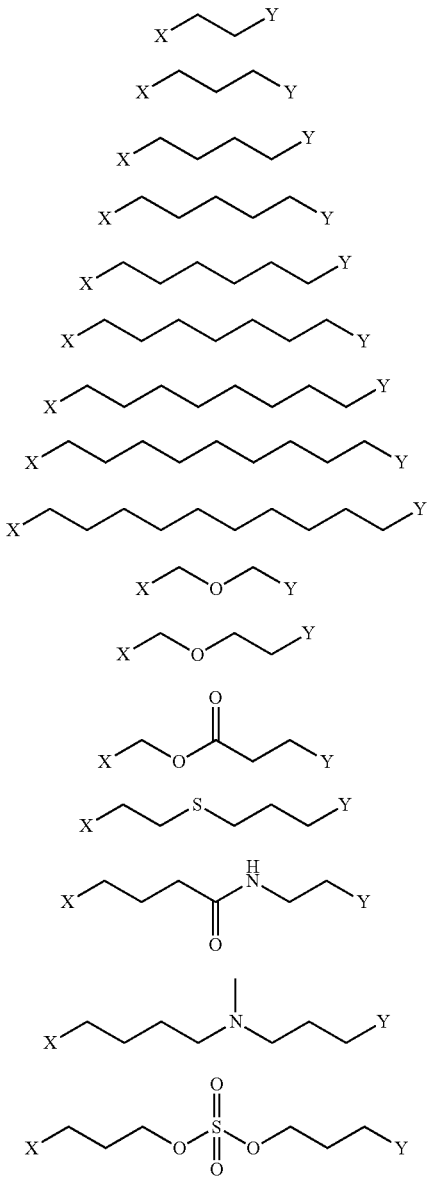

TABLE 8-continued

Exemplary X—L₂—Y groups of the invention.

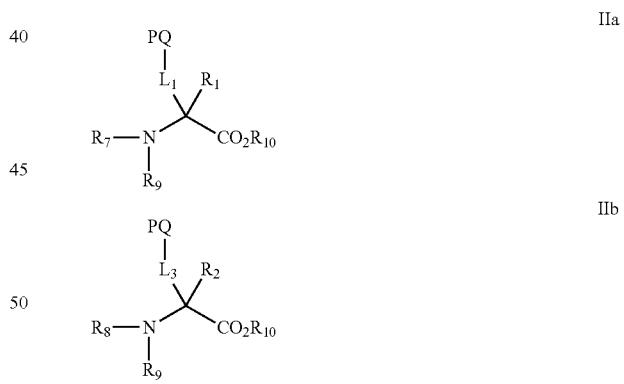

Each X and Y in this Table, are, for example, independently Cl—, Br— or I—.

Kits

In another aspect, the present invention further provides kits comprising amino acid analogs and/or macrocycle-forming linkers as described herein.

In one embodiment the kit contains a) a compound of Formulas IIa and a compound of Formula IIb:

IIa

IIb wherein $R_1$ is alkyl, alkenyl, alkynyl, arylalkyl, cycloalkyl, heteroalkyl, or heterocycloalkyl, unsubstituted or substituted with halo-;

$R_2$ is —H, alkyl, alkenyl, alkynyl, arylalkyl, cycloalkyl, heteroalkyl, or heterocycloalkyl, unsubstituted or substituted with halo-;

$L_1$ and $L_3$ are independently alkylene, alkenylene, alkynylene, heteroalkylene, cycloalkylene, heterocycloalkylene, cycloarylene, or heterocycloarylene or [—$R_4$—K—$R_4$-]n, each being unsubstituted or substituted with $R_5$;

K is O, S, SO, $SO_2$, CO, $CO_2$, or $CONR_3$;

R₄ is alkylene, alkenylene, alkynylene, heteroalkylene, cycloalkylene, heterocycloalkylene, arylene, or heteroarylene;

each R₅ is independently halogen, alkyl, —OR₆, —N(R₆)₂, —SR₆, —SOR₆, —SO₂R₆, —CO₂R₆, —R₆, a fluorescent moiety, a radioisotope, or a therapeutic agent;

each R₆ is independently —H, alkyl, alkenyl, alkynyl, arylalkyl, cycloalkylalkyl, heteroalkylalkyl, heterocyclyalkyl, a fluorescent moiety, a radioisotope, or a therapeutic agent;

R₇ and R₈ are independently —H, alkyl, alkenyl, alkynyl, arylalkyl, cycloalkylalkyl, heteroalkylalkyl, or heterocyclyalkyl;

R₉ and R₁₀ are each independently —H or any protecting group suitable for liquid or solid phase peptide synthesis; Q is S;

P is —H, -trityl, p-methoxytrityl, —S t-butyl, or any other protecting group suitable for liquid or solid phase peptide synthesis; or Q and P when taken together form a moiety capable of undergoing chemical transformation into an —SH group; n is an integer from 1 to 5;

and b) a macrocycle-forming linker of the structure:

wherein L₂ is alkylene, alkenylene, alkynylene, heteroalkylene, cycloalkylene, heterocycloalkylene, cycloarylene, heterocycloarylene, or [—R₁₁—K—R₁₁-]n, each being unsubstituted or substituted with R₁₂;

each R₁₁ is alkylene, alkenylene, alkynylene, heteroalkylene, cycloalkylene, heterocycloalkylene, arylene, or heteroarylene;

each R₁₂ is independently halogen, alkyl, —OR₁₃, —N(R₆)₁₃, —SR₁₃, —SOR₁₃, —SO₂R₁₃, —CO₂R₁₃, —R₁₃, a fluorescent moiety, a radioisotope, or a therapeutic agent;

each R₁₃ is independently —H, alkyl, alkenyl, alkynyl, arylalkyl, cycloalkylalkyl, heteroalkylalkyl, heterocyclyalkyl, a fluorescent moiety, a radioisotope, or a therapeutic agent; and X and Y are each independently a reactive group capable of reacting with a thiol group.

In some embodiments, the kit comprises one or more containers holding one or more naturally-occurring amino acids or amino acid analogs as described herein. In other embodiments, the kit comprises one or more containers holding one or more macrocycle-forming linkers as described herein. In yet other embodiments, the kit comprises one or more containers holding one or more amino acids or amino acid analogs as described herein, as well as one or more containers holding one or more macrocycle-forming linkers as described herein.

For example, in some embodiments, the kit comprises a container holding at least one amino acid or amino acid analog, as described above, having an —SH moiety, the amino acid optionally protected and suitable for the syntheses described herein. In some embodiments, the amino acid or amino acid analog is selected from the group consisting of L-cysteine, D-cysteine, L-N-methylcysteine, D-N-methylcysteine, L-homocysteine, D-homocysteine, L-N-methylhomocysteine, D-N-methylhomocysteine, α-methyl-L-cysteine, α-methyl-D-cysteine, α-methyl-L-homocysteine, α-methyl-D-homocysteine, L-penicillamine, D-penicillamine, L-N-methylpenicillamine, D-N-methylpenicillamine and all forms suitably protected for liquid or solid phase peptide synthesis.

In some embodiments, the kit comprises a container holding at least one naturally-occurring amino acid, non-naturally-occurring amino acid, or amino acid analog bound to a solid support compatible with the syntheses described herein for peptidomimetic macrocycles.

In some embodiments, the kit comprises a container holding a macrocycle-forming linker as described above. In some embodiments, the kit further comprises one or more containers holding reagents necessary for the macrocyclization reactions described herein, such as trifluoroacetic acid, liquid ammonia, NH₃/MeOH, NH₃/DMF, mercaptoethanol, hindered bases such as triethylamine or diisopropylethylamine, and guanidinium HCl.

In some embodiments, the kit comprises one container holding an amino acid analog of the invention including a reactive —SH group in combination with a container holding a macrocycle-forming linker of the invention. Optionally, the kit further comprises one or more containers holding reagents necessary for the macrocyclization reaction. In other embodiments, the kit comprises two containers, each of which holds a different amino acid analog of the invention including a reactive —SH group. Optionally, the kit further comprises one or more containers holding reagents necessary for the macrocyclization reaction and/or a macrocycle-forming linker of the invention.

Assays

The properties of the peptidomimetic macrocycles of the invention are assayed, for example, by using the methods described below. In some embodiments, a macrocycle of the invention has enhanced properties relative to a corresponding non-macrocyclic polypeptide. A corresponding non-macrocyclic polypeptide is, for example, a precursor of a peptidomimetic macrocycle, such as a compound of Formula III which is converted into said macrocycle. Alternatively, a corresponding non-macrocyclic polypeptide is a polypeptide sequence, such as a natural polypeptide sequence which has substantial sequence overlap with the macrocycle of the invention. Numerous examples of natural polypeptides corresponding to the macrocyclic polypeptide are shown in Tables 1, 2, 3 and 4.

In general, a corresponding non-macrocyclic polypeptide can also be a labeled natural polypeptide or peptidomimetic precursor. Such labeling, for example by fluorescent or radioactive labeling, is used if necessary in some of the assays described below. In such assays, both the macrocycle and the corresponding non-macrocyclic polypeptide are typically labeled by similar or functionally equivalent methods.

Assay to Determine Alpha Helicity.

The percent helicity of unmodified pro-apoptotic BH3 domains are predominantly random coils in solution, with α-helical content usually under 25%. Peptidomimetic macrocycles with optimized linkers, on the other hand, possess, for example, an alpha-helicity that is at least two-fold greater than that of a corresponding non-macrocyclic polypeptide. In some embodiments, macrocycles of the invention will possess an alpha-helicity of greater than 50%. To assay the helicity of peptidomimetic macrocycles of the invention, such as BH3 domain-based macrocycles, the compounds are dissolved in aqueous 50 mM potassium phosphate solution at pH 7, or distilled H₂O, to concentrations of 25-50 μM. Circular dichroism (CD) spectra are obtained on a spectropolarimeter (e.g., Jasco J-710) at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The a helical content of each peptide is calculated by dividing the mean residue ellipticity [φ]222 obs by the reported [D]222 obs for a model helical decapeptide (Yang et al. (1986), Methods Enzymol. 130:208)).

Assay to Determine Melting Temperature (Tm).

A peptidomimetic macrocycle of the invention comprising a secondary structure such as an α-helix exhibits, for example, a higher melting temperature than a corresponding non-macrocyclic polypeptide. Typically peptidomimetic macrocycles of the invention exhibit Tm of >60° C. representing a highly stable structure in aqueous solutions. Peptidomimetic macrocycles and unmodified peptides are dissolved in distilled $H_2O$ at final concentration of 50 μM and the Tm is determined by measuring the change in ellipticity over a temperature range (4 to 95° C.) on a spectropolarimeter (e.g., Jasco J-710) using the following measurement parameters: wavelength 222 nm; step resolution, 0.5 nm; speed, 20 nm/sec; accumulations, 10; response, 1 sec; bandwidth, 1 nm; temperature increase rate: 1° C./min; path length, 0.1 cm.

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention are subjected to in vitro trypsin proteolysis to assess for any change in degradation rate compared to a corresponding non-macrocyclic polypeptide. The peptidomimetic macrocycle and a corresponding non-macrocyclic polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and precursor peptide (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time (k=−1× slope).

Ex Vivo Stability Assay.

Peptidomimetic macrocycles with optimized linkers possess, for example, an ex vivo half-life that is at least two-fold greater than that of a corresponding non-macrocyclic polypeptide peptide, and possess an ex vivo half-life of 12 hours or more. For ex vivo serum stability studies, a peptidomimetic macrocycle and a corresponding non-macrocyclic polypeptide (in a specific example, the corresponding natural polypeptide) (2 mcg) are incubated with fresh mouse, rat and human serum (2 mL) at 37° C. for 0, 1, 2, 4, 8, and 24 hours. To determine the level of intact compound, the following procedure is used: The samples are extracted by transferring 100 μl of sera to 2 ml centrifuge tubes followed by the addition of 10 μL of 50% formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis.

In vitro Binding Assays.

To assess the binding and affinity of peptidomimetic macrocycles and precursor peptides to acceptor proteins, a fluorescence polarization assay (FPA) isused, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a Perkin-Elmer LS50B luminescence spectrophotometer. Kd values are determined by nonlinear regression analysis using Graphpad Prism software. A peptidomimetic macrocycle of the invention show, for example, similar or lower Kd than a corresponding non-macrocyclic polypeptide.

Acceptor proteins for BH3-peptides such as BCL-2, BCL-$X_L$, BAX or MCL1 can be used in this assay. Acceptor proteins for p53 peptides such as MDM2 or MDMX can be used in this assay.

In vitro Displacement Assays to Characterize Antagonists of Peptide-Protein Interactions.

To assess the binding and affinity of compounds that antagonize the interaction between a peptide (e.g. a BH3 peptide or a p53 peptide) and an acceptor protein, a fluorescence polarization assay (FPA) utilizing a fluoresceinated peptidomimetic macrocycle derived from a precursor peptide sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a Perkin-Elmer LS50B luminescence spectrophotometer. Kd values are determined by nonlinear regression analysis using Graphpad prism software.

Any class of molecule, such as small organic molecules, peptides, oligonucleotides or proteins can be examined as putative antagonists in this assay. Acceptor proteins for BH3-peptides such as BCL2, BCL-XL, BAX or MCL1 can be used in this assay. Acceptor proteins for p53 peptides such as MDM2 or MDMX can be used in this assay.

Binding Assays in Intact Cells.

It is possible to measure binding of peptides or peptidomimetic macrocycles to their natural acceptors in intact cells by immunoprecipitation experiments. For example, intact cells are incubated with fluoresceinated (FITC-labeled) compounds for 4 hrs in the absence of serum, followed by serum replacement and further incubation that ranges from 4-18 hrs. Cells are then pelleted and incubated in lysis buffer (50 mM Tris [pH 7.6], 150 mM NaCl, 1% CHAPS and protease inhibitor cocktail) for 10 minutes at 4° C. Extracts are centrifuged at 14,000 rpm for 15 minutes and supernatants collected and incubated with 10 μl goat anti-FITC antibody for 2 hrs, rotating at 4° C. followed by further 2 hrs incubation at 4° C. with protein A/G Sepharose (50 μl of 50% bead slurry). After quick centrifugation, the pellets are washed in lysis buffer containing increasing salt concentration (e.g., 150, 300, 500 mM).

The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the peptidomimetic macrocycle, including BCL2, MCL1, BCL-XL, A1, BAX, BAK, MDM2 or MDMX.

Cellular Permeability Assays.

A peptidomimetic macrocycle is, for example, more cell permeable compared to a corresponding non-macrocyclic polypeptide. In some embodiments, the peptidomimetic macrocycles are more cell permeable than a corresponding non-macrocyclic polypeptides. Peptidomimetic macrocycles with optimized linkers possess, for example, cell permeability that is at least two-fold greater than a corresponding non-macrocyclic polypeptide, and often 20% or more of the applied peptide will be observed to have penetrated the cell after 4 hours. To measure the cell permeability of peptidomimetic macrocycles and corresponding non-macrocyclic polypeptides, intact cells are incubated with fluoresceinated peptidomimetic macrocycles or corresponding non-macrocyclic polypeptides (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KINETICSCAN® HCS Reader (an automated device for analysis of cellular and intracellular spatial parameters, over time, in populations of living cells).

Cellular Efficacy Assays.

The efficacy of certain peptidomimetic macrocycles is determined, for example, in cell-based killing assays using a variety of tumorigenic and non-tumorigenic cell lines and primary cells derived from human or mouse cell populations. Cell viability is monitored, for example, over 24-96 hrs of incubation with peptidomimetic macrocycles (0.5 to 50 µM) to identify those that kill at EC50<10 µM. Several standard assays that measure cell viability are commercially available and are optionally used to assess the efficacy of the peptidomimetic macrocycles. In addition, assays that measure Annexin V and caspase activation are optionally used to assess whether the peptidomimetic macrocycles kill cells by activating the apoptotic machinery.

In Vivo Stability Assay.

To investigate the in vivo stability of the peptidomimetic macrocycles, the compounds are, for example, administered to mice and/or rat by IV, IP, PO or inhalation routes at concentrations ranging from 0.1 to 50 mg/Kg and blood specimens withdrawn at 0', 5', 15', 30', 1 hr, 4 hrs, 8 hrs and 24 hours post-injection. Levels of intact compound in 25 µL of fresh serum are then measured by LC-MS/MS as above.

In vivo Efficacy in Animal Models.

To determine the anti-oncogenic activity of the certain peptidomimetic macrocycles in vivo, the compounds are, for example, given alone (IP, W, PO, by inhalation or nasal routes) or in combination with sub-optimal doses of relevant chemotherapy (e.g., cyclophosphamide, doxorubicin, etoposide). In one example, $5\times10^6$ RS4; 11 cells (established from the bone marrow of a patient with acute lymphoblastic leukemia) that stably express luciferase are injected by tail vein in NOD-SCID mice 3 hrs after they have been subjected to total body irradiation. If left untreated, this form of leukemia is fatal in 3 weeks in this model. The leukemia is readily monitored, for example, by injecting the mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (10 days after injection/day 1 of experiment, in bioluminescence of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation of DoHH2, a cell line derived from human follicular lymphoma, into NOD-SCID mice that stably expresses luciferase. These in vivo tests optionally generate preliminary pharmacokinetic, pharmacodynamic and toxicology data.

Clinical Trials.

To determine the suitability of the peptidomimetic macrocycles of the invention for treatment of humans, clinical trials are performed. For example, patients diagnosed with cancer and in need of treatment are selected and separated in treatment and one or more control groups, wherein the treatment group is administered a peptidomimetic macrocycle of the invention, while the control groups receive a placebo or a known anti-cancer drug. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocyle show improved long-term survival compared to a patient control group treated with a placebo.

Pharmaceutical Compositions and Routes of Administration

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

Methods of Use

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the p53 MDM2 system, labeled stabilized peptidomimetic macrocyles based on the p53 is used in an MDM2 binding assay along with small molecules that competitively bind to MDM2. Competitive binding studies allow for rapid in vitro evaluation and determination of drug candidates specific for the p53/MDM2 system. Likewise in the BH3/BCL-$X_L$ anti-apoptotic system labeled peptidomimetic macrocycles based on BH3 can be used in a BCL-$X_L$ binding assay along with small molecules that competitively bind to BCL-$X_L$. Competitive binding studies allow for rapid in vitro evaluation and determination of drug candidates specific for the BH3/BCL-$X_L$ system. The invention further provides for the generation of antibodies against the peptidomimetic macrocycles. In some embodiments, these antibodies specifically bind both the peptidomimetic macrocycle and the p53 or BH3 precursor peptides upon which the peptidomimetic macrocycles are derived. Such antibodies, for example, disrupt the p53/MDM2 or BH3/BCL-XL systems, respectively.

In other aspects, the present invention provides for both prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities). It is believed that some BCL-2 type disorders are caused, at least in part, by an abnormal level of one or more BCL-2 family members (e.g., over or under expression), or by the presence of one or more BCL-2 family members exhibiting abnormal activity. As such, the reduction in the level and/or activity of the BCL-2 family member or the enhancement of the level and/or activity of the BCL-2 family member, is used, for example, to ameliorate or reduce the adverse symptoms of the disorder.

In another aspect, the present invention provides methods for treating or preventing hyperproliferative disease by interfering with the interaction or binding between p53 and MDM2 in tumor cells. These methods comprise administering an effective amount of a compound of the invention to a warm blooded animal, including a human, or to tumor cells containing wild type p53. In some embodiments, the administration of the compounds of the present invention induce cell growth arrest or apoptosis. In other or further embodiments, the present invention is used to treat disease and/or tumor cells comprising elevated MDM2 levels. Elevated levels of MDM2 as used herein refers to MDM2 levels greater than those found in cells containing more than the normal copy number (2) of mdm2 or above about 10,000 molecules of MDM2 per cell as measured by ELISA and similar assays (Picksley et al. (1994), *Oncogene* 9, 2523 2529).

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, he peptidomimetics macrocycles of the invention is used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetics macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML), and chronic myelogenous leukemia (CML) (reviewed in Vaickus (1991), *Crit Rev. Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In other or further embodiments, the peptidomimetics macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia In other or further embodiments, the peptidomimetics macrocycles of the invention that act to decrease apoptosis are used to treat disorders associated with an undesirable level of cell death. Thus, in some embodiments, the anti-apoptotic peptidomimetics macrocycles of the invention are used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic peptidomimetics macrocycles of the invention are used, in some embodiments, in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In other or further embodiments, the anti-apoptotic peptidomimetics macrocycles of the invention are used to treat all such disorders associated with undesirable cell death.

Some examples of immunologic disorders that are treated with the peptidomimetics macrocycles described herein include but are not limited to organ transplant rejection, arthritis, lupus, IBD, Crohn's disease, asthma, multiple sclerosis, diabetes, etc.

Some examples of neurologic disorders that are treated with the peptidomimetics macrocycles described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

Some examples of endocrinologic disorders that are treated with the peptidomimetics macrocycles described herein include but are not limited to diabetes, hypothyroidism, hypopituitarism, hypoparathyroidism, hypogonadism, etc.

Examples of cardiovascular disorders (e.g., inflammatory disorders) that are treated or prevented with the peptidomimetics macrocycles of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

EXAMPLES

The following section provides illustrative examples of the present invention.

Example 1

Synthesis of a peptidomimetic macrocycle. The target molecule is the BID-BH3peptide with amino acids 12 and 16 replaced by Cysteine (see Table 1 and Table 6). The Cysteine side chain thiols are then derivatized with 1,4-dibromobutane to form the bis-thioether peptidomimetic macrocycle (DIIR-NIARHLACVGDCN$_L$DRSI is disclosed as SEQ ID NO: 99)

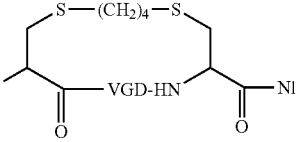

Following the general peptide synthetic strategy described, the peptidomimetic precursor was a polypeptide of the sequence DIIRNIARHLACVGDCN$_L$DRSI (SEQ ID NO: 100) (where "N$_L$" or "Nle" represent norleucine) synthesized at 0.2 mmol scale on a PTI-Ranin PS3 single channel synthesizer using the following coupling cycles for each amino acid:

Deprotection 20% piperidine in DMF 2×7 min
Wash DMF 6×0.5 min
Coupling 5 fold excess each of amino acid, TBTU and DIEA in DMF 1×20 min
Wash DMF 2×0.5 min
Coupling 5 fold excess each of amino acid, TBTU and DIEA in DMF 1×20 min
Wash DMF 6×0.5 min The precursor polypeptide was acetylated at the amino terminus by treatment with 1 mM acetic anhydride and 1 mM diisopropylethylamine (DIEA) in dimethylformamide (DMF) for 45 minutes. Synthesis was done on rink amide resin (substitution 0.6 mMol/g) with the cys$^9$ and cys$^{13}$ thiols protected with p-methoxytrityl (Mmt) groups. The Mmt groups were selectively deprotected with 1% TFA/4% TIS in dichloromethane (DCM) and the polypeptide was alkylated overnight at room temperature using 50 molar equivalents of 1,4-dibromobutane and 13 molar equivalents of diisopropylethylamine (DIEA) in dichloroethane. The peptide was then cleaved from the resin by treatment with 94% TFA 2% TIS 2% Anisole 2% H$_2$O for 3 hours followed by filtration, concentration by rotary evaporation and precipitation with diethyl ether. The expected molecular weight of the final peptidomimetic macrocycle product is 2448.91. The observed molecular weight is 2445.5 by MALDI MS (see FIG. 1).

A number of embodiments of the invention have been described. Nevertheless, it will be understood that various modifications may be made without departing from the spirit and scope of the invention. Accordingly, other embodiments are within the scope of the following claims.

What is claimed is:

1. A peptidomimetic macrocycle of Formula (I):

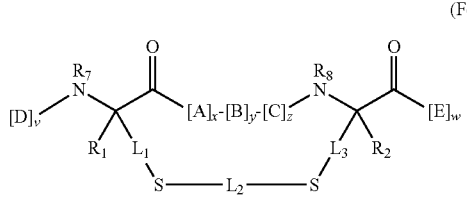
(Formula I)

wherein:
each A, C, D, and E is independently a natural or non-natural amino acid;
each B is independently a natural or non-natural amino acid,

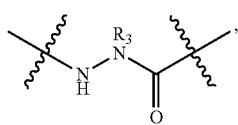

[—NH-$L_4$-CO—], [—NH-$L_4$-$SO_2$—], or [—NH-$L_4$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;
each $R_3$ is independently hydrogen, alkyl, alkenyl, alkynyl, arylalkyl, heteroalkyl, cycloalkyl, heterocycloalkyl, cycloalkylalkyl, cycloaryl, or heterocycloaryl, unsubstituted or substituted with $R_5$;
$L_1$, $L_3$ and $L_4$ are independently alkylene, alkenylene, alkynylene, heteroalkylene, heterocycloalkylene, or [—$R_4$—K—$R_4$—]n, each being unsubstituted or substituted with $R_5$;
$L_2$ is a linker moiety unsubstituted or substituted with $R_5$;
each K is independently O, S, SO, $SO_2$, CO, $CO_2$, or $CONR_3$;
each $R_4$ is independently alkylene, alkenylene, alkynylene, heteroalkylene, cycloalkylene, heterocycloalkylene, arylene, or heteroarylene;
each $R_5$ is independently halogen, alkyl unsubstituted or substituted with halogen, —$OR_6$, —$N(R_6)_2$, —$SR_6$, —$SOR_E$, —$SO_2R_6$, —$CO_2R_6$, a fluorescent label, a radioisotope or a therapeutic agent;
each $R_6$ is independently —H, alkyl, alkenyl, alkynyl, arylalkyl, cycloalkylalkyl, heterocycloalkyl, a fluorescent label, a radioisotope or a therapeutic agent;
$R_7$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with a D residue;
$R_8$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with an E residue;
v is an integer from 1-1000;
w is an integer from 1-1000;
x is an integer from 0-10;
y is an integer from 0-10;
z is an integer from 0-10;
each n is independently an integer from 1-5; and
x+y+z is at least 3,
wherein at least one of A, B, C, D, or E, is an amino acid with a side chain thiol moiety.

2. The peptidomimetic macrocycle of claim 1, wherein at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-.

3. The peptidomimetic macrocycle of claim 1, wherein at least one of $R_1$ and $R_2$ is hydrogen.

4. The peptidomimetic macrocycle of claim 1, wherein at least one of D and E is attached to an additional macrocycle-forming linker of the formula [-$L_1$-S-$L_2$-S-$L_3$-].

5. The peptidomimetic macrocycle of claim 1, wherein [-$L_1$-S-$L_2$-S-$L_3$-] spans from 1 turn to 5 turns of an alpha-helix.

6. The peptidomimetic macrocycle of claim 1, wherein $L_2$ is cycloarylene or heterocycloarylene, each of which is unsubstituted or substituted with $R_5$.

7. The peptidomimetic macrocycle of claim 1, wherein $L_2$ is substituted with $R_5$.

8. The peptidomimetic macrocycle of claim 1, wherein $L_2$ is aryl.

9. The peptidomimetic macrocycle of claim 7, wherein $R_5$ is halogen.

10. The peptidomimetic macrocycle of claim 7, wherein $R_5$ is haloalkyl.

11. The peptidomimetic macrocycle of claim 1, wherein D is an amino acid with a side chain thiol moiety.

12. The peptidomimetic macrocycle of claim 11, wherein D is cysteine.

13. The peptidomimetic macrocycle of claim 1, wherein E is an amino acid with a side chain thiol moiety.

14. The peptidomimetic macrocycle of claim 13, wherein E is cysteine.

15. The peptidomimetic macrocycle of claim 1, wherein A, B, or C is an amino acid with a side chain thiol moiety.

16. The peptidomimetic macrocycle of claim 1, wherein A, B, or C is cysteine.

17. The peptidomimetic macrocycle of claim 1, wherein one of D is attached to an additional macrocycle-forming linker of the formula [-$L_1$-S-$L_2$-S-$L_3$-].

18. The peptidomimetic macrocycle of claim 1, wherein one of E is attached to an additional macrocycle-forming linker of the formula [-$L_1$-S-$L_2$-S-$L_3$-].

19. The peptidomimetic macrocycle of claim 1, wherein one of D is attached to an additional macrocycle-forming linker of the formula [-$L_1$-S-$L_2$-S-$L_3$-] and one of E is attached to an additional macrocycle-forming linker of the formula [-$L_1$-S-$L_2$-S-$L_3$-].

20. The peptidomimetic macrocycle of claim 1, wherein both $R_1$ and $R_2$ are hydrogen.

21. A method for synthesizing a peptidomimetic macrocycle, comprising contacting a peptidomimetic precursor of Formula III:

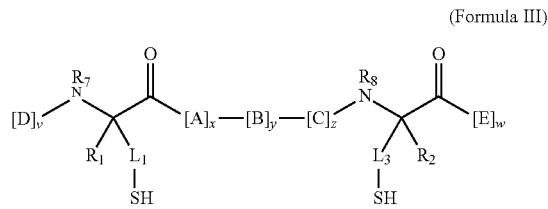
(Formula III)

with a compound of formula X-L$_2$-Y,
wherein
each A, C, D, and E is independently a natural or non-natural amino acid;
  each B is independently a natural or non-natural amino acid, amino acid analog,

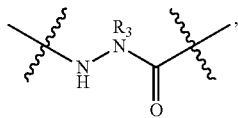

[—NH-L$_4$-CO—], [—NH-L$_4$-SO$_2$—], or [—NH-L$_4$-];
R$_1$ and R$_2$ are independently —H, alkyl, alkenyl, alkynyl, arylalkyl, cycloalkyl, cycloalkylalkyl, heteroalkyl, or heterocycloalkyl, each of which except —H is unsubstituted or substituted with halo-;
each R$_3$ is independently —H, alkyl, alkenyl, alkynyl, arylalkyl, heteroalkyl, cycloalkyl, heterocycloalkyl, cycloalkylalkyl, cycloaryl, or heterocycloaryl, each of which except —H is unsubstituted or substituted with R$_5$;
L$_1$, L$_3$, and L$_4$ are independently alkylene, alkenylene, alkynylene, heteroalkylene, cycloalkylene, heterocycloalkylene, cycloarylene, heterocycloarylene, or [—R$_4$—K—R$_4$—]$_n$, each being unsubstituted or substituted with R$_5$;
L$_2$ is a linker moiety unsubstituted or substituted with R$_5$;
each K is independently O, S, SO, SO$_2$, CO, CO$_2$, or CONR$_3$;
each R$_4$ is independently alkylene, alkenylene, alkynylene, heteroalkylene, cycloalkylene, heterocycloalkylene, arylene, or heteroarylene;
each R$_5$ is independently halogen, alkyl unsubstituted or substituted with halogen, —OR$_6$, —N(R$_6$)$_2$, —SR$_6$, —SOR$_6$, —SO$_2$R$_6$, —CO$_2$R$_6$, a fluorescent moiety, a radioisotope, or a therapeutic agent;
each R$_6$ is independently —H, alkyl, alkenyl, alkynyl, arylalkyl, cycloalkylalkyl, heterocycloalkyl, a fluorescent moiety, a radioisotope, or a therapeutic agent;
R$_7$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is unsubstituted or substituted with R$_5$, or part of a cyclic structure with a D residue;
R$_8$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is unsubstituted or substituted with R$_5$, or part of a cyclic structure with an E residue;
v is an integer from 1-1000;
w is an integer from 1-1000;
x is an integer from 0-10;
y is an integer from 0-10;
z is an integer from 0-10; and
wherein at least one of A, B, C, D, or E, is an amino acid with a side chain thiol moiety; and X and Y are each independently a reactive group capable of reacting with a thiol group; and further wherein the contacting results in formation of the peptidomimetic macrocycle.

* * * * *